(12) United States Patent
Chen et al.

(10) Patent No.: US 11,549,131 B2
(45) Date of Patent: Jan. 10, 2023

(54) BIOSYNTHETIC PRODUCTION OF GAMMA-LACTONES

(71) Applicant: Conagen Inc., Bedford, MA (US)

(72) Inventors: Hui Chen, Bedford, MA (US); Oliver Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 17/150,774

(22) Filed: Jan. 15, 2021

(65) Prior Publication Data

US 2021/0261991 A1    Aug. 26, 2021

Related U.S. Application Data

(63) Continuation of application No. PCT/US2019/042300, filed on Jul. 17, 2019.

(60) Provisional application No. 62/758,019, filed on Nov. 9, 2018, provisional application No. 62/699,374, filed on Jul. 17, 2018.

(51) Int. Cl.
    *C12P 17/04*  (2006.01)
    *C12N 15/52*  (2006.01)

(52) U.S. Cl.
    CPC .............. *C12P 17/04* (2013.01); *C12N 15/52* (2013.01)

(58) Field of Classification Search
    CPC .................................. C12N 15/52; C12P 17/04
    See application file for complete search history.

(56) References Cited

U.S. PATENT DOCUMENTS

| | | | |
|---|---|---|---|
| 2,936,310 A | 5/1960 | Beets et al. | |
| 3,890,353 A | 6/1975 | Becker | |
| 7,863,023 B2 * | 1/2011 | Zucca | C12P 17/04 435/126 |
| 8,420,833 B2 | 4/2013 | Katz et al. | |
| 9,970,037 B2 | 5/2018 | Tang et al. | |
| 2003/0055105 A1 | 3/2003 | Ito et al. | |
| 2005/0130278 A1 | 6/2005 | Mitsuhashi et al. | |
| 2008/0293101 A1 | 11/2008 | Peters et al. | |
| 2010/0285546 A1 | 11/2010 | Liao et al. | |
| 2022/0106618 A1 | 4/2022 | Chen et al. | |

FOREIGN PATENT DOCUMENTS

| | | |
|---|---|---|
| CA | 1221105 A | 4/1987 |
| CN | 108300608 A | 7/2018 |
| CN | 111533888 A | 8/2020 |
| DE | 1025861 B2 | 3/1958 |
| JP | H01104187 A | 4/1989 |
| JP | H026516 B2 | 2/1990 |
| JP | H0412718 B2 | 3/1992 |
| JP | H0710234 B2 | 2/1995 |
| JP | 2005-065658 A | 3/2005 |
| JP | 2010-163366 A | 7/2010 |
| JP | 2011-083264 A | 4/2011 |
| JP | 2013-128440 A | 7/2013 |
| JP | 5474360 B2 | 4/2014 |
| WO | WO 2009/030672 A1 | 3/2009 |
| WO | WO 2017/137935 A1 | 8/2017 |
| WO | WO 2018/005806 A2 | 1/2018 |
| WO | WO 2018/046104 A1 | 3/2018 |
| WO | WO 2009/134899 A2 | 11/2019 |
| WO | WO 2020/018729 A1 | 1/2020 |
| WO | WO 2021/071896 A1 | 4/2021 |

OTHER PUBLICATIONS

An et al., Increased production of γ-lactones from hydroxy fatty acids by whole Waltomyces lipofer cells induced with oleic acid. Appl Microbiol Biotechnol., 2013, vol. 97: 8265-8272. (Year: 2013).*
Sadowski et al., The sequence-structure relationship and protein function prediction. Current Opinion in Structural Biology, 2009, vol. 19: 357-362. (Year: 2009).*
Sanchez-Sevilla et al., Deciphering gamma-decalactone biosynthesis in strawberry fruit using a combination of genetic mapping, RNA-Seq and eQTL analyses. BMC Genomics, 2014, vol. 15:218, pp. 1-15. (Year: 2014).*
Seffernick et al., Melamine deaminase and Atrazine chlorohydrolase: 98 percent identical but functionally different. J. Bacteriol., 2001, vol. 183 (8): 2405-2410. (Year: 2001).*
Tang et al., Identification of Dehalobacter reductive dehydrogenases that catalyse dechlorination of chloroform, 1,1,1-trichloroethane and 1,1-dichloroethane. Phil Trans R Soc B, 2013, vol. 368: Mar. 18, 2012, pp. 1-10. (Year: 2013).*
Wache et al., Optimization of Yarrowia lipolytica's beta-oxidation pathway for gamma-decalactone production. Journal of Molecular Catalysis B: Enzymatic 19-20, 2002: 347-351 (Year: 2002).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
PCT/US2019/042300, Oct. 29, 2019, International Search Report and Written Opinion.
PCT/US2019/042300, Jan. 28, 2021, International Preliminary Report on Patentability.
No Author Listed, GenBank Accession No. GAN03094, version GAN03094.1. NADPH—cytochrome P450 reductase [Mucor ambiguus]. Submitted Feb. 10, 2015. 2 pages.
Alberdi-Cedeño et al., A new methodology capable of characterizing most volatile and less volatile minor edible oils components in a single chromatographic run without solvents or reagents. Detection of new components. Food Chemistry. Apr. 15, 2017;221:1135-1144. doi: 10.1016/j.foodchem.2016.11.046. Epub Nov. 9, 2016.
Herzner et al., Larvae of the parasitoid wasp *Ampulex compressa* sanitize their host, the American cockroach, with a blend of antimicrobials. Proc Natl Acad Sci U S A. Jan. 22, 2013;110(4):1369-74. doi: 10.1073/pnas.1213384110. Epub Jan. 7, 2013.

(Continued)

*Primary Examiner* — Ganapathirama Raghu
(74) *Attorney, Agent, or Firm* — Wolf, Greenfield & Sacks, P.C.; W. John Keyes

(57) ABSTRACT

Provided herein are methods for making gamma lactones comprising reacting a carboxylic acid substrate with a heterologous cytochrome P450 (CYP450) protein with carboxylic acid 4-hydroxylase activity.

12 Claims, 8 Drawing Sheets

Specification includes a Sequence Listing.

(56) References Cited

OTHER PUBLICATIONS

Ray et al., (R)-Desmolactone is a Sex Pheromone or Sex Attractant for the Endangered Valley Elderberry Longhorn Beetle *Desmocerus californicus dimorphus* and Several Congeners (Cerambycidae: Lepturinae). PLoS One. 2014; 9(12): e115498/1-18.10.1371/journal. pone.0115498.

Schlutt et al., Sensory-directed identification of creaminess-enhancing volatiles and semivolatiles in full-fat cream. Agric Food Chem. Nov. 14, 2007;55(23):9634-45. doi: 10.1021/jf0721545. Epub Oct. 13, 2007.

Genbank Submission. NCBI; Accession No. ORZ20503, version ORZ20503.1. Cytochrome P450 [Absidia repens]. Mondo et al.; Apr. 20, 2017. 2 Pages.

Genbank Submission. NCBI; Accession No. XP_003663647, version XP_003663647.1. Uncharacterized protein MYCTH_101224 [Thermothelomyces thermophiles ATCC 42464]. Berka et al.; Nov. 27, 2019. 12 Pages.

Dietrich et al., Altering the regioselectivity of the subterminal fatty acid hydroxylase P450 BM-3 towards gamma- and delta-positions. J Biotechnol. Jan. 1, 2009;139(1):115-7. doi: 10.1016/j.jbiotec.2008. 10.002. Epub Oct. 15, 2008.

Endrizzi et al., Bioconversion of methyl ricinoleate to 4-hydroxydecanoic acid and to gamma-decalactone by yeasts of the genus *Candida*. J Basic Microbiol. 1995;35(5):285-92. doi: 10.1002/jobm. 3620350503.

Nagel et al., Diverging Mechanisms: Cytochrome-P450-Catalyzed Demethylation and γ-Lactone Formation in Bacterial Gibberellin Biosynthesis. Angew Chem Int Ed Engl. May 22, 2018;57(21):6082-6085. doi: 10.1002/anie.201713403. Epub Apr. 26, 2018.

Nyktel-Szymańska et al., Elimination and detoxification of 2,4-D by Umbelopsis isabellina with the involvement of cytochrome P450. Environ Sci Pollut Res Int. Jan. 2018;25(3):2738-2743. doi: 10.1007/s11356-017-0571-4. Epub Nov. 14, 2017.

No Author Listed, 11-Dodecanolide. CAS No. 95338-31-1. Mar. 27, 2005. 17 pages.

[No Author Listed], NADPH—cytochrome P450 reductase. Uniprot No. A0A0C9M7Q9. entered Apr. 29, 2015. 3 pages.

Anadon et al., Scientific Opinion on Flavouring Group Evaluation 10, Revision 2 (FGE.10Rev2): Aliphatic primary and secondary saturated and unsaturated alcohols, aldehydes, acetals, carboxylic acids and esters containing an additional oxygenated functional group and lactones from chemical groups 9, 13 and 301. EFSA Journal. 2011; 9(7):2164.

Becker et al., Eine neuartige Fragmentierung bicyclischer Enolather Verfahren zur Darstellung macrocyclischer Lactone. Helvetica Chimica Acta. 1971; 54: 2889-95.

Bersuker et al., Origin of Musk Fragrance Activity: The Electron-Topologic Approach. New Journal of Chemistry. 1991; 15: 307-20.

Bestmann et al., Neue Synthese makrocyclischer Lactone. Angewandte Chemie. Jan. 1983; 95(10): 810-11. https://doi.org/10.1002/ange.19830951024.

Boddupalli et al., Fatty acid monooxygenation by P450BM-3: product identification and proposed mechanisms for the sequential hydroxylation reactions. Arch Biochem Biophys. Jan. 1992;292(1):20-8. doi: 10.1016/0003-9861(92)90045-x.

Gargouri et al., Synthesis of a novel macrolactone by lipase-catalyzed intra-esterification of hydroxy-fatty acid in organic media. J Biotechnol. Jan. 18, 2002;92(3):259-66. doi: 10.1016/s0168-1656(01)00374-1.

Guo et al., Enzymic synthesis of macrocyclic lactones. J Am Chem Soc. 1988; 110(6): 1999-2001.

Hayes, The Catalytic Activity of Lipases Toward Hydroxy Fatty Acids—A Review. J Amer Oil Chem Soc. 1996; 73: 543-549. https://doi.org/10.1007/BF02518105.

Hinkamp et al., Selective w to (w—2)-Chlorination of Fatty Acids by Way of Adsorption on Alumina. Liebigs Annalen der Chemie. 1992; 1992: 559-563.

Hötling et al., Identification of a Grain Beetle Macrolide Pheromone and its Synthesis by Ring-Closing Metathesis Using a Terminal Alkyne. Org Lett. Oct. 16, 2015;17(20):5004-7. doi: 10.1021/acs. orglett.5b02461. Epub Sep. 25, 2015.

Krow, The Baeyer-Villiger Oxidation of ketones and aldehydes. Chapter 3 in: Organic Reactions. vol. 43. 1993. John Wiley & Sons, Inc., Eds. pp. 329-331.

Meng et al., Enzymatic cascade biosynthesis reaction of musky macrolactones from fatty acids. Enzyme Microb Technol. Dec. 2019;131:109417. doi: 10.1016/j.enzmictec.2019.109417. Epub Aug. 27, 2019.

Schulz et al., An Antiaphrodisiac in *Heliconius melpomene* Butterflies. J Chem Ecol. Jan. 2008;34(1):82-93. doi: 10.1007/s10886-007-9393-z. Epub Dec. 12, 2007.

Stepurko et al., Thermodynamic Analysis of the Polymerization of Methyl-Substituted Lactones. Fibre Chemistry. 2014; 46: 80-89. https://doi.org/10.1007/s10692-014-9566-9.

Stoll et al., Multimembered heterocyclic compounds. VIII. Higher mono- and polylactone rings. Helvetica Chimica Acta. 1935; 18: 1087-1125.

Stoll et al., Polymembered heterocyclic compounds. VI. Preparation of pure ambrettolide. Preparation of 12-hydroxystearic and 14-hydroxypentadecanoic acid lactones. Helvetica Chimica Acta. 1934; 17: 1609-12.

Todea et al., Selectivity of lipases for estolides synthesis. Pure and Applied Chemistry. 2015; 87(1): 51-58. https://doi.org/10.1515/pac-2014-0716.

Wasserman et al., Activated carboxylates from the photooxygenation of oxazoles : Application to the synthesis of recifeiolide, curvularin and other macrolides. Tetrahedron. 1981; 37,(23): 4059-67. https://doi.org/10.1016/S0040-4020(01)93281-8.

Wu et al., Volatile components of fruits of Ligustrum lucidum Ait. stimulate proliferation and differentiation of rat calvarial osteoblasts. African Journal of Biotechnology. Aug. 10, 2011; 10(43): 8662-68. DOI: 10.5897/AJB11.214.

* cited by examiner

BIOSYNTHETIC PRODUCTION OF GAMMA-LACTONES

RELATED APPLICATIONS

This application is a continuation of PCT/US2019/042300, filed Jul. 17, 2019, which claims priority to and the benefit of U.S. Provisional Application No. 62/699,374, filed on Jul. 17, 2018, and U.S. Provisional Application No. 62/758,019, filed on Nov. 9, 2018, the disclosure of each of which is hereby incorporated by reference in its entirety.

FIELD OF THE INVENTION

The field of the invention relates to methods and processes for producing gamma-lactones via recombinant proteins and/or microbial cultures modified to express such recombinant proteins. More specifically, the present disclosure relates to the production of C4-C20 gamma-lactones from corresponding carboxylic acid substrates via enzymatic conversion.

BACKGROUND

There exists a universal desire for foods, fragrances and cosmetics that have pleasant tastes and odors. In many cases, these traits of pleasant smells and tastes are provided through various lactone compounds, including various gamma lactones, that possess desirable aroma and flavor characteristics. Current demand for lactone compounds is mainly addressed through either chemical synthesis or extraction processes from plants. Plant extraction-based production has significant disadvantages, such as weather effects on the strength and abundance of the compounds of interest, risk of plant diseases and/or poor harvest, stability of the compound, environmental impact of increased production and trade restrictions. Industrial production can cause environmental damage, may use dangerous precursors and itself may be subject to increased costs due to the costs of key substrates.

Accordingly, there is a need in the art for novel methods to produce gamma lactones economically and reliably without the limitations posed by plant extraction and chemical synthesis.

SUMMARY OF THE INVENTION

According to the current invention, gamma-lactones may be reliably produced at high yield by gene modification and fermentation technology using microorganisms such as bacteria and/or yeasts. These microorganisms are able to synthesize lactones de novo or by biotransformation of fatty acids to provide commercially significant yields. Hence, new production methods are provided herein to reduce costs of gamma-lactone production and lessen the environmental impact of large-scale cultivation and processing of natural sources from which these lactone compounds can be extracted.

More specifically, the present disclosure encompasses methods and compositions for making gamma-lactones by microbial fermentation, wherein the microbial fermentation comprises a cellular system expressing a heterologous cytochrome P450 (CYP450) protein.

The present disclosure is based, in part, on the finding that certain CYP450 proteins and functional variants thereof have hydroxylase activity specifically at the carbon atom positioned gamma to the carbonyl carbon of a carboxylic acid substrate, thereby generating a 4-hydroxy carboxylic acid which upon acidification can convert into a gamma-lactone spontaneously. By overexpressing these CYP450 proteins in a modified microbial system and feeding into it the appropriate carboxylic acid substrates, various gamma-lactones can be produced at high titers. The present disclosure, therefore, provides economical and reliable methods for producing gamma-lactones from carboxylic acids (e.g., various commercially available fatty acids) without the disadvantages associated with chemical synthesis or plant extraction.

Accordingly, one aspect of the present disclosure provides a method for producing a C4-C20 gamma lactone comprising (a) incubating a cellular system expressing a heterologous CYP450 protein in a medium comprising a C4-C20 carboxylic acid substrate to provide a 4-hydroxy C4-C20 carboxylic acid, and (b) subjecting the 4-hydroxy C4-C20 carboxylic acid to acidic conditions to produce the C4-C20 gamma lactone. In some embodiments, the 4-hydroxy carboxylic acid can be isolated from the cellular system prior to acidification.

In various embodiments, the cellular system can be a transformed host cell comprising a sequence that encodes the heterologous CYP450 protein. In some embodiments, the cellular system can comprise bacterial cells, yeast cells, plant cells that do not naturally produce the lactone of interest, algal cells, and/or fungal cells that do not naturally encode the specified fungal CYP450 protein described herein. In particular embodiments, the cellular system can comprise transformed bacteria and/or yeast cells selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Mucor; Pantoea; Corynebacterium*; and *Clostridium*. In some embodiments, the cellular system can comprise growing cells. In other embodiments, the cellular system can comprise resting cells (e.g., lyophilized cells that have been frozen then re-suspended).

The present disclosure also encompasses a method for producing a C4-C20 gamma lactone, wherein the method involves providing a reaction mixture including a recombinant CYP450 protein described herein and a C4-C20 carboxylic acid substrate to provide a 4-hydroxy C4-C20 carboxylic acid, and subjecting the 4-hydroxy C4-C20 carboxylic acid to acidic conditions to produce the C4-C20 gamma lactone. In some embodiments, the recombinant CYP450 protein can be expressed by a transformed host cell in the reaction mixture. In other embodiments, the recombinant CYP450 protein can be isolated then provided in the reaction mixture.

In various embodiments of the methods for producing a C4-C20 gamma lactone according to the present disclosure, the CYP450 protein can be a *Mucor ambiguous* CYP450 protein or a functional variant thereof that has carboxylic acid 4-hydroxylase activity. For example, the CYP450 protein can comprise an amino acid sequence having at least 80%, 85%, 90%, 95%, 96%, 97%, 98%, or 99% identity to SEQ ID NO: 1. In certain embodiments, the CYP450 protein can comprise the amino acid sequence of SEQ ID NO: 1. In other embodiments, the CYP450 protein can consist of the amino acid sequence of SEQ ID NO: 1. Accordingly, the transformed host cell transformed to express such a CYP450 protein or variant thereof can comprise a nucleotide sequence having at least 80%, 85%, 90%, 95%, 97%, 98%, or 99% identity to SEQ ID NO: 2.

In some other embodiments, the CYP450 protein can be a *Basidiobolus meristosporus* CYP450 protein or a functional variant thereof that has carboxylic acid 4-hydroxylase activity. For example, the CYP450 protein can comprise an amino acid sequence having at least 80%, 85%, 90%, 95%, 96%, 97%, 98%, or 99% identity to SEQ ID NO: 3. In certain embodiments, the CYP450 protein can comprise the amino acid sequence of SEQ ID NO: 3. In other embodiments, the CYP450 protein can consist of the amino acid sequence of SEQ ID NO: 3. Accordingly, the transformed host cell transformed to express such a CYP450 protein or variant thereof can comprise a nucleotide sequence having at least 80%, 85%, 90%, 95%, 97%, 98%, or 99% identity to SEQ ID NO: 4.

In yet other embodiments, the CYP450 protein can be a *Umbelopsis isabellina* CYP450 protein or a functional variant thereof that has carboxylic acid 4-hydroxylase activity. For example, the CYP450 protein can comprise an amino acid sequence having at least 80%, 85%, 90%, 95%, 96%, 97%, 98%, or 99% identity to SEQ ID NO: 5. In certain embodiments, the CYP450 protein can comprise the amino acid sequence of SEQ ID NO: 5. In other embodiments, the CYP450 protein can consist of the amino acid sequence of SEQ ID NO: 5. Accordingly, the transformed host cell transformed to express such a CYP450 protein or variant thereof can comprise a nucleotide sequence having at least 80%, 85%, 90%, 95%, 97%, 98%, or 99% identity to SEQ ID NO: 6.

In some embodiments, the C4-C20 carboxylic acid substrate can include a C4-C20 carboxylic acid; a salt of a C4-C20 carboxylic acid; an ester of a C4-C20 carboxylic acid; a mono-, di- or triglyceride of a C4-C20 carboxylic acid; or a combination thereof. In certain embodiments, the C4-C20 carboxylic acid substrate can be a C4-C20 carboxylic acid or a salt thereof. The C4-C20 carboxylic acid can be a straight-chain C4-C20 carboxylic acid, a branched C4-C20 carboxylic acid, a saturated C4-C20 carboxylic acid, or an unsaturated C4-C20 carboxylic acid. The C4-C20 carboxylic acid can be optionally substituted with one or more functional groups selected from a hydroxyl group and an amino group, provided that such optional substitution is not at the carbon atoms that are positioned alpha, beta, or gamma to the carbonyl carbon of the carboxylic acid (see FIG. 1). In certain embodiments, the C4-C20 carboxylic acid can be a straight-chain fully saturated carboxylic acid. In particular embodiments, the C4-C20 carboxylic acid substrate can be selected from hexanoic acid, hexenoic acid, heptanoic acid, 1-heptenoic acid, 2-heptenoic acid, octanoic acid, 1-octenoic acid, 2-octenoic acid, 3-octenoic acid, nonanoic acid, 1-nonenoic acid, 2-nonenoic acid, 3-nonenoic acid, decanoic acid, 1-decenoic acid, 2-decenoic acid, 3-decenoic acid, undecanoic acid, 1-undecenoic acid, 2-undecenoic acid, 3-undecenoic acid, dodecanoic acid, 1-dodecenoic acid, 2-dodecenoic acid, 3-dodecenoic acid, tridecanoic acid, 1-tridecenoic acid, 2-tridecenoic acid, 3-tridecenoic acid, tetradecanoic acid, 1-tetradecenoic acid, 2-tetradecenoic acid, and 3-tetradecenoic acid.

Depending on the identity of the C4-C20 carboxylic acid substrate, the gamma lactones produced by the present methods can comprise a C4-C20 gamma lactone selected from γ-hexalactone, γ-hexenolactone, γ-heptalactone, γ-heptenolactone, γ-octalactone, γ-octenolactone, γ-nonalactone, γ-nonenolactone, γ-decalactone, γ-decenolactone, γ-undecalactone, γ-undecenolactone, γ-dodecalactone, γ-dodecenolactone, γ-tridecalactone, γ-tridecenolactone, γ-tetradecalactone, and γ-tetradecenolactone.

Any methods described herein may further comprise isolating the gamma lactones from the cellular system to provide a crude product. In some embodiments, the crude product obtained from such isolating step can include a lactone content that is at least 70% pure. In some embodiments, the method further comprises purifying a crude product comprising the gamma lactones. In some embodiments, said crude product is purified by column chromatography. In some embodiments, said crude product is purified by acid-base extraction. In some embodiments, said crude product is purified by vacuum distillation. In some embodiments, the method further comprises purifying said lactones using a semi-preparative HPLC.

The gamma lactones produced by the methods described herein can be used alone or mixed with other lactones, flavors, or scents to obtain a desired composition for use in a variety of consumer products or foods. For example, the gamma lactones described herein can be included in food products (such as beverages, soft drinks, ice cream, dairy products, confectioneries, cereals, chewing gum, baked goods, etc.), dietary supplements, medical nutrition, as well as pharmaceutical products to give desired flavor or aromatic characteristics. In some embodiments, the disclosure provides a consumable product comprising a flavoring or scented amount of a lactone produced by any one of the methods above or described elsewhere herein for use in a specific flavoring context, formula or recipe. In some embodiments, the consumable product can be a food, beverage, perfume, or cosmetic product. In some embodiments, the composition can be selected from beverages, confectioneries, bakery products, cookies, and chewing gums. In certain embodiments, the composition can be a food, beverage, perfume, or cosmetic product having a flavor or aroma profile designed to taste or smell like: peach, apricot, pear, maple, coconut, vanilla, butterscotch, grenadine and/or date.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 2a shows the production of γ-heptalactone (GC7) from enanthic acid (heptanoic acid, C7). FIG. 2b shows the production of γ-octalactone (GC8) from caprylic acid (octanoic acid, C8). FIG. 2c shows the production of γ-nonalactone (GC9) from pelargonic acid (nonanoic acid, C9). FIG. 2d shows the production of γ-decalactone (GC10) from capric acid (decanoic acid, C10). FIG. 2e shows the production of γ-undecalactone (GC11) from undecylic acid (undecanoic acid, C11). FIG. 2f shows the production of γ-dodecalactone (GC12) from lauric acid (dodecanoic acid, C12). FIG. 2g shows the production of γ-tridecalactone (GC13) from tridecylic acid (tridecanoic acid, C13). FIG. 2h shows the production of γ-tetradecalactone (GC14) from myristic acid (tetradecanoic acid, C14).

FIG. 4a shows the production of γ-hexalactone (GC6) from hexanoic acid (C6). FIG. 4b shows the production of γ-heptalactone (GC7) from enanthic acid (heptanoic acid, C7). FIG. 4c shows the production of γ-decalactone (GC10) from capric acid (decanoic acid, C10). FIG. 4d shows the production of γ-undecalactone (GC11) from undecylic acid (undecanoic acid, C11). FIG. 4e shows the production of γ-dodecalactone (GC12) from lauric acid (dodecanoic acid, C12). FIG. 4f shows the production of γ-tridecalactone (GC13) from tridecylic acid (tridecanoic acid, C13). FIG. 4g shows the production of γ-tetradecalactone (GC14) from myristic acid (tetradecanoic acid, C14).

DETAILED DESCRIPTION

Figure 1:
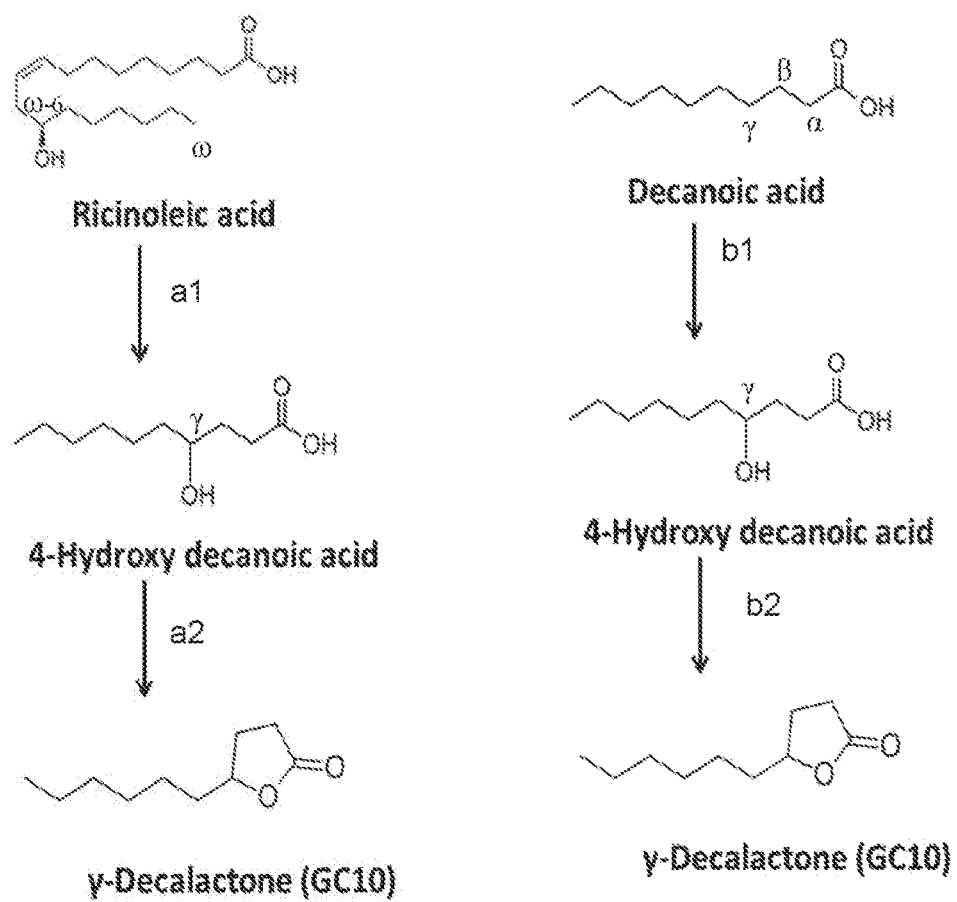
FIG. 1 compares the 4-hydroxylase route against the β-oxidation route for producing gamma-lactones from carboxylic acid substrates. Specifically, the production of γ-decalactone (GC10) is used as an example to illustrate the two routes.
Figure 2A:
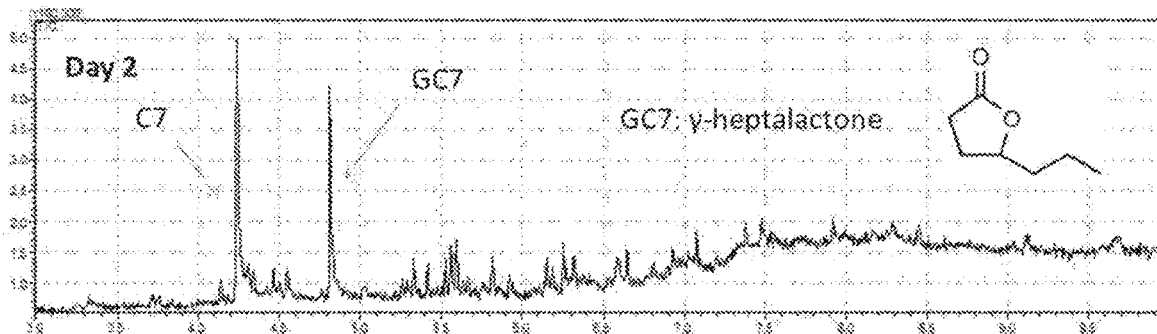
FIGS. 2a-2h show GC/MS spectra confirming production of various γ-lactones using an *E. coli* culture transformed to overexpress *Mucor ambiguus* P450. Specifically.
Figure 2B:
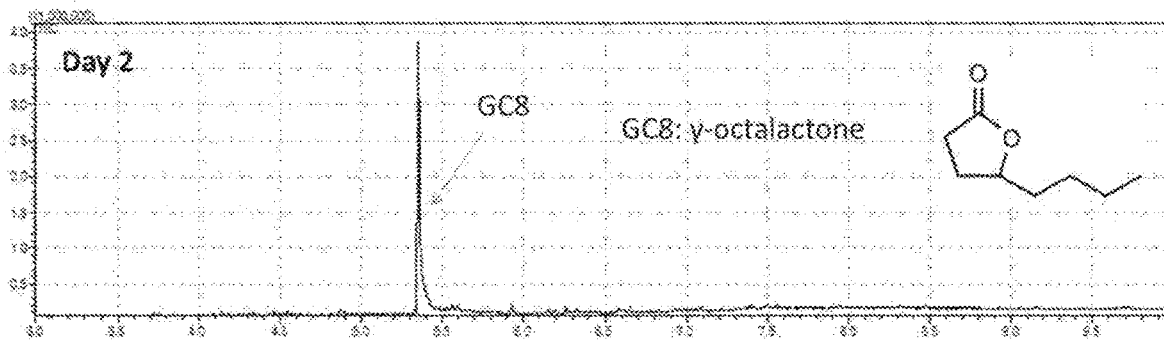
Figure 2C:
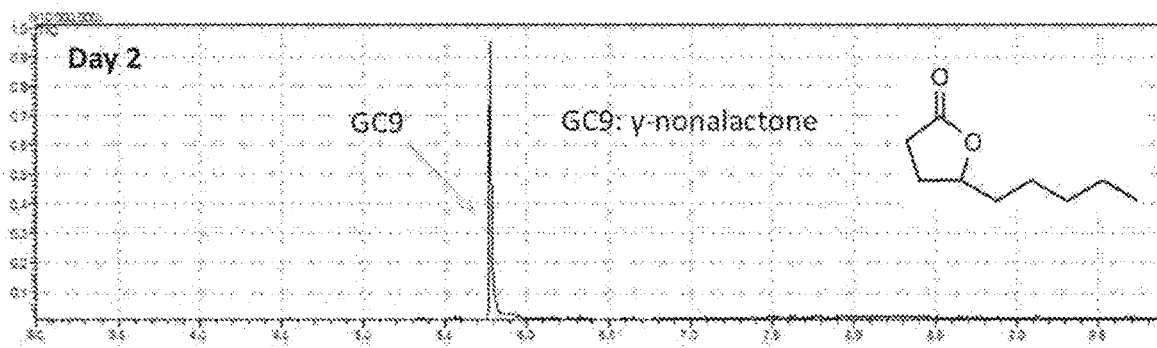
Figure 2D:
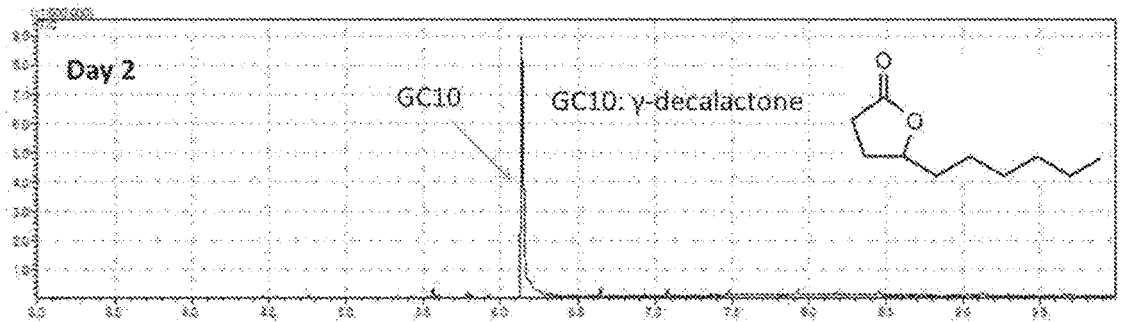
Figure 2E:
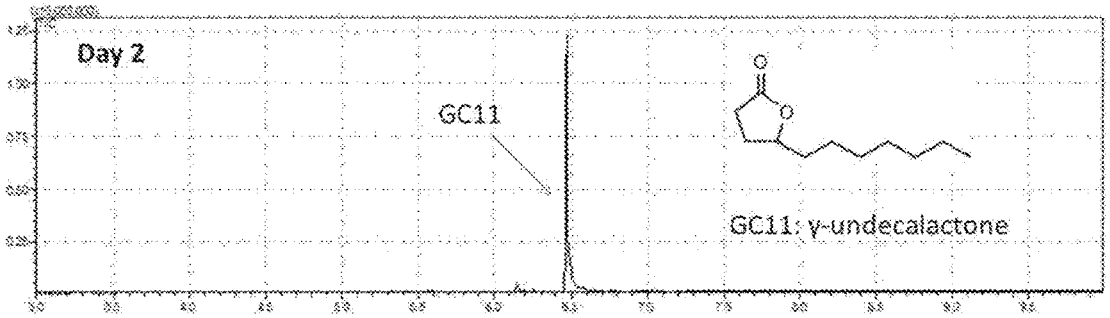
Figure 2F:
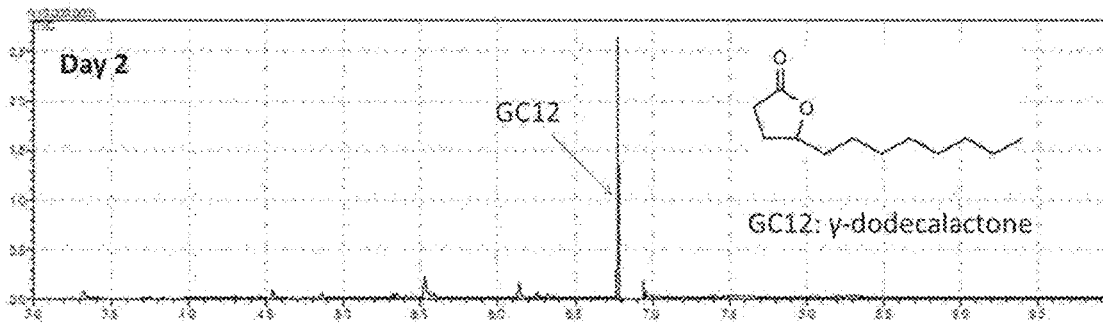
Figure 2G:
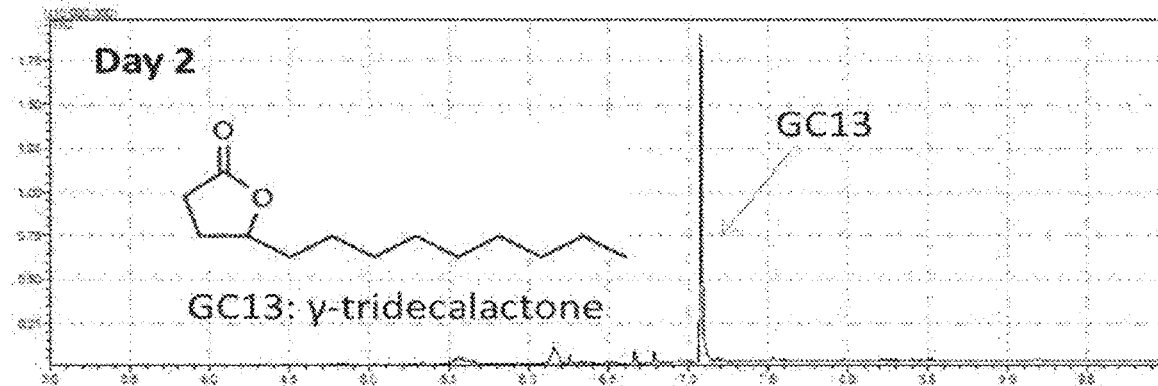
Figure 2H:
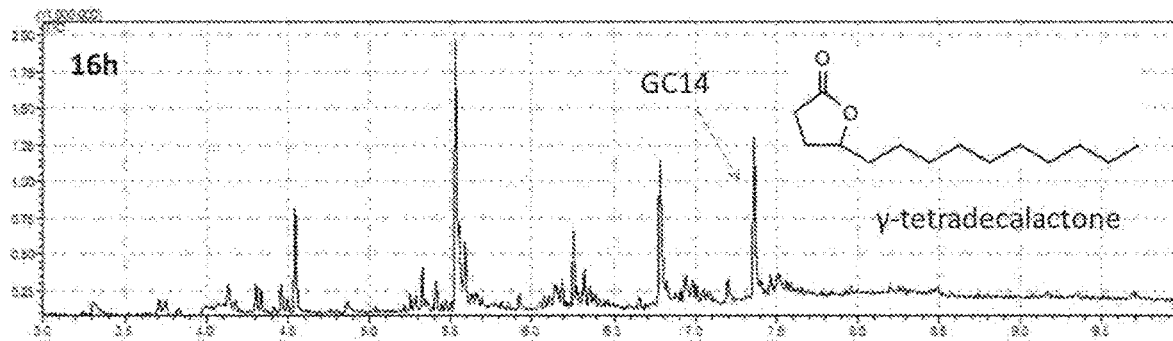

Referring to FIG. 1, biosynthetic production of gamma lactones from fatty acids can be performed via at least two different routes. According to the β-oxidation route, a medium-chain (C6-C12) or long-chain fatty acid (C13 to C21) having a hydroxyl group close to the omega carbon (e.g., ω-1, ω-2, ω-3, ω-4, ω-5, ω-6 etc.) can be incubated with a yeast to cause multiple cycle of β-oxidation (step a1), with each β-oxidation cycle removing a C2 residue from the hydrocarbon backbone fragment between the hydroxylated carbon atom and the carbonyl carbon atom. Depending whether there is an odd or even number of carbon atoms within such hydrocarbon backbone fragment, a 4-hydroxy (gamma-hydroxy) or a 5-hydroxy (delta-hydroxy) fatty acid may result, and upon lactonization under acidic conditions (step a2), either a gamma lactone or a delta lactone is produced.

By comparison, the present method makes use of cytochrome P450 proteins that have been specifically identified with 4-hydroxylase activity. Carboxylic acids or derivatives thereof can be bioconverted by such cytochrome P450 proteins into 4-hydroxy carboxylic acids (step b1), which upon acidification (step b2), produce the corresponding gamma lactone. The present methods, therefore, provide an economical and reliable approach for producing gamma lactones that is suitable for commercial scale-up production.

Methods of Making Lactones

Methods described herein, in some embodiments, provide for the production of C4-C20 gamma lactones from a C4-C20 carboxylic acid substrate. In some embodiments, methods of making such gamma lactones comprise (a) incubating a cellular system expressing a heterologous cytochrome P450 (CYP450) protein with a C4-C20 carboxylic acid substrate to provide a 4-hydroxy C4-C20 carboxylic acid, and (b) contacting or otherwise subjecting the 4-hydroxy carboxylic acid to acidic conditions to produce the C4-C20 gamma lactone.

In some embodiments, methods of making the lactones comprise incubating cell pellets harvested from the cellular system expressing the heterologous CYP450 protein with the carboxylic acid substrate. In some embodiments, methods of making the lactones comprise incubating resuspended cell pellets harvested from the cellular system with the carboxylic acid substrate.

Methods of making gamma lactones described herein comprise incubating a cellular system expressing a heterologous CYP450 protein in a medium comprising the carboxylic acid substrate at any ratio. In some embodiments, methods of making gamma lactones comprise incubating a cellular system comprising between 1 gram of cells per liter to 200 grams of cells per liter (1 g/L to 200 g/L) of the medium. The medium can include between 1 gram of carboxylic acid substrate per liter to 20 grams of fatty acids per liter (1 g/L to 20 g/L). In some embodiments, methods of making lactones comprise incubating a cellular system comprising 100 grams of cells per liter (100 g/L) in a medium that includes 1 gram of carboxylic acid substrate per liter (1 g/L).

In some embodiments, methods of making lactones comprise incubating a cellular system with a medium comprising the carboxylic acid substrate for a suitable period sufficient for the formation of 4-hydroxy carboxylic acid. In some embodiments, methods of making lactones comprise contacting the 4-hydroxy carboxylic acids with a cell culture for a suitable period sufficient for formation of gamma lactones in the cell culture. In some embodiments, methods of making lactones comprise isolating the 4-hydroxy carboxylic acids prior to contact with the cell culture. In some embodiments, methods of making lactones comprise incubating the 4-hydroxy carboxylic acids in a medium with the cell culture.

Methods of making lactones described herein encompass incubating (e.g., incubating a cellular system expressing a heterologous CYP450 protein with a medium comprising the appropriate carboxylic acid substrate) for an amount of time. In some embodiments, methods of making lactones comprise incubating for a time between 0.5 hour to 96 hours.

Methods of making lactones described herein encompass incubating (e.g., incubating a cellular system expressing a heterologous CYP450 protein with a medium comprising the appropriate carboxylic acid substrate) at a temperature. In some embodiments, methods of making lactones comprise incubating at a temperature between 16° C. to 40° C.

Cytochrome P450

Cytochrome P450 (CYP450) proteins, generally, are enzymes that catalyze oxidation of substrates. CYP450 proteins are members of the hemeprotein superfamily, and contain heme as a cofactor. CYP450 enzymes have been identified in many organisms including, but not limited to, animals, plants, fungi, bacteria, archaea, and viruses. However, to the inventors' knowledge, previous to the current invention, CYP450 enzymes having specific carboxylic acid 4-hydroxylase activity have not been reported.

After performing rigorous high-throughput screening of large libraries of candidate genes for fungal cytochrome P450 enzymes with carboxylic acid 4-hydroxylase activity, the inventors have identified certain CYP450 genes that show high carboxylic acid 4-hydroxylase activity.

A CYP450 protein suitable for use in the present methods can be a *Mucor ambiguous* CYP450 protein or a functional variant thereof that has carboxylic acid 4-hydroxylase activity. Specifically, the CYP450 protein can comprise an amino acid sequence having at least 80%, 85%, 90%, 95%, 96%, 97%, 98%, or 99% identity to SEQ ID NO: 1. In certain embodiments, the CYP450 protein can comprise the amino acid sequence of SEQ ID NO: 1. In other embodiments, the CYP450 protein can consist of the amino acid sequence of SEQ ID NO: 1. Accordingly, the cellular system used to express such heterologous CYP450 protein can comprise host cells having a nucleotide sequence having at least 80%, 85%, 90%, 95%, 97%, 98%, or 99% identity to SEQ ID NO: 2.

In some other embodiments, the CYP450 protein can be a *Basidiobolus meristosporus* CYP450 protein or a functional variant thereof that has carboxylic acid 4-hydroxylase activity. For example, the CYP450 protein can comprise an amino acid sequence having at least 80%, 85%, 90%, 95%, 96%, 97%, 98%, or 99% identity to SEQ ID NO: 3. In certain embodiments, the CYP450 protein can comprise the amino acid sequence of SEQ ID NO: 3. In other embodiments, the CYP450 protein can consist of the amino acid sequence of SEQ ID NO: 3. Accordingly, the cellular system used to express such heterologous CYP450 protein can comprise host cells having a nucleotide sequence having at least 80%, 85%, 90%, 95%, 97%, 98%, or 99% identity to SEQ ID NO: 4.

In yet other embodiments, the CYP450 protein can be a *Umbelopsis isabelline* CYP450 protein or a functional variant thereof that has carboxylic acid 4-hydroxylase activity. For example, the CYP450 protein can comprise an amino acid sequence having at least 80%, 85%, 90%, 95%, 96%, 97%, 98%, or 99% identity to SEQ ID NO: 5. In certain embodiments, the CYP450 protein can comprise the amino acid sequence of SEQ ID NO: 5. In other embodiments, the CYP450 protein can consist of the amino acid sequence of SEQ ID NO: 5. Accordingly, the cellular system used to express such heterologous CYP450 protein can comprise host cells having a nucleotide sequence having at least 80%, 85%, 90%, 95%, 97%, 98%, or 99% identity to SEQ ID NO: 6.

Carboxylic Acid Substrates

According to methods described herein, a C4-C20 carboxylic acid substrate can be converted to 4-hydroxy carboxylic acids. The carboxylic acid substrate can be a carboxylic acid and/or a derivative thereof. For example, the C4-C20 carboxylic acid substrate can include a C4-C20 carboxylic acid; a salt of a C4-C20 carboxylic acid; an ester of a C4-C20 carboxylic acid; a mono-, di- or triglyceride of a C4-C20 carboxylic acid; or a combination thereof. As used herein, C4-C20 denotes an organic compound having 4-20 carbon atoms. The range expressed by C4-C20 is meant to convey any ranges therewithin, including but not limited to C5-C20, C6-C20, C7-C20, C8-C20, C9-C20, C10-C20, C6-C14, C7-C14, C8-C14, C9-C14, C10-C14 etc. Accordingly, the carboxylic acid substrate described herein can include a carboxylic acid or a derivative thereof having 4, 5, 6, 7, 8, 9, 10, 11, 12, 13, 14, 15, 16, 17, 18, 19, or 20 carbon atoms. In certain embodiments, the C4-C20 carboxylic acid substrate can be a C4-C20 carboxylic acid or a salt thereof. Without limitation, the substrate acid can be in the form of its sodium salt, potassium salt, calcium salt, magnesium salt, ammonium salt, and the like.

The C4-C20 carboxylic acid can be a straight-chain C4-C20 carboxylic acid, a branched C4-C20 carboxylic acid, a saturated C4-C20 carboxylic acid, or an unsaturated C4-C20 carboxylic acid. The C4-C20 carboxylic acid can be optionally substituted with one or more functional groups selected from a hydroxyl group and an amino group, provided that such optional substitution is not at the carbon atoms that are positioned alpha, beta, or gamma to the carbonyl carbon of the carboxylic acid (see FIG. 1). In certain embodiments, the C4-C20 carboxylic acid can be a straight-chain fully saturated carboxylic acid.

Examples of C4-C20 carboxylic acids include, but are not limited to, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid, hexatriacontanoic acid, heptatriacontanoic acid, octatriacontanoic acid, nonatriacontanoic acid, and tetracontanoic acid. Table 1 provides common names, structural formulas, and lipid numbers of exemplary fatty acids.

TABLE 1

Examples of fatty acids.

| Common Name | Systematic Name | Structural Formula | Lipid Numbers |
| --- | --- | --- | --- |
| Valeric acid | Pentanoic acid | $CH_3(CH_2)_3COOH$ | C5:0 |
| Caproic acid | Hexanoic acid | $CH_3(CH_2)_4COOH$ | C6:0 |
| Enanthic acid | Heptanoic acid | $CH_3(CH_2)_5COOH$ | C7:0 |
| Caprylic acid | Octanoic acid | $CH_3(CH_2)_6COOH$ | C8:0 |
| Pelargonic acid | Nonanoic acid | $CH_3(CH_2)_7COOH$ | C9:0 |
| Capric acid | Decanoic acid | $CH_3(CH_2)_8COOH$ | C10:0 |
| Undecylic acid | Undecanoic acid | $CH_3(CH_2)_9COOH$ | C11:0 |
| Lauric acid | Dodecanoic acid | $CH_3(CH_2)_{10}COOH$ | C12:0 |
| Tridecylic acid | Tridecanoic acid | $CH_3(CH_2)_{11}COOH$ | C13:0 |
| Myristic acid | Tetradecanoic acid | $CH_3(CH_2)_{12}COOH$ | C14:0 |
| Pentadecylic acid | Pentadecanoic acid | $CH_3(CH_2)_{13}COOH$ | C15:0 |
| Palmitic acid | Hexadecanoic acid | $CH_3(CH_2)_{14}COOH$ | C16:0 |
| Margaric acid | Heptadecanoic acid | $CH_3(CH_2)_{15}COOH$ | C17:0 |
| Stearic acid | Octadecanoic acid | $CH_3(CH_2)_{16}COOH$ | C18:0 |

TABLE 1-continued

Examples of fatty acids.

| Common Name | Systematic Name | Structural Formula | Lipid Numbers |
|---|---|---|---|
| Nonadecylic acid | Nonadecanoic acid | $CH_3(CH_2)_{17}COOH$ | C19:0 |
| Arachidic acid | Eicosanoic acid | $CH_3(CH_2)_{18}COOH$ | C20:0 |
| Heneicosylic acid | Heneicosanoic acid | $CH_3(CH_2)_{19}COOH$ | C21:0 |
| Behenic acid | Docosanoic acid | $CH_3(CH_2)_{20}COOH$ | C22:0 |
| Tricosylic acid | Tricosanoic acid | $CH_3(CH_2)_{20}COOH$ | C23:0 |
| Lignoceric acid | Tetracosanoic acid | $CH_3(CH_2)_{22}COOH$ | C24:0 |
| Pentacosylic acid | Pentacosanoic acid | $CH_3(CH_2)_{23}COOH$ | C25:0 |
| Cerotic acid | Hexacosanoic acid | $CH_3(CH_2)_{24}COOH$ | C26:0 |
| Heptacosylic acid | Heptacosanoic acid | $CH_3(CH_2)_{25}COOH$ | C27:0 |
| Montanic acid | Octacosanoic acid | $CH_3(CH_2)_{26}COOH$ | C28:0 |
| Nonacosylic acid | Nonacosanoic acid | $CH_3(CH_2)_{27}COOH$ | C29:0 |
| Melissic acid | Triacontanoic acid | $CH_3(CH_2)_{28}COOH$ | C30:0 |
| Henatriacontylic acid | Henatriacontanoic acid | $CH_3(CH_2)_{29}COOH$ | C31:0 |
| Lacceroic acid | Dotriacontanoic acid | $CH_3(CH_2)_{30}COOH$ | C32:0 |
| Psyllic acid | Tritriacontanoic acid | $CH_3(CH_2)_{31}COOH$ | C33:0 |
| Geddic acid | Tetratriacontanoic acid | $CH_3(CH_2)_{32}COOH$ | C34:0 |
| Ceroplastic acid | Pentatriacontanoic acid | $CH_3(CH_2)_{33}COOH$ | C35:0 |
| Hexatriacontylic acid | Hexatriacontanoic acid | $CH_3(CH_2)_{34}COOH$ | C36:0 |
| Heptatriacontanoic acid | Heptatriacontanoic acid | $CH_3(CH_2)_{35}COOH$ | C37:0 |
| Octatriacontanoic acid | Octatriacontanoic acid | $CH_3(CH_2)_{36}COOH$ | C38:0 |
| Nonatriacontanoic acid | Nonatriacontanoic acid | $CH_3(CH_2)_{37}COOH$ | C39:0 |
| Tetracontanoic acid | Tetracontanoic acid | $CH_3(CH_2)_{38}COOH$ | C40:0 |

Examples of unsaturated C4-C20 carboxylic acids include hexenoic acid, 1-heptenoic acid, 2-heptenoic acid, 1-octenoic acid, 2-octenoic acid, 3-octenoic acid, 1-nonenoic acid, 2-nonenoic acid, 3-nonenoic acid, 1-decenoic acid, 2-decenoic acid, 3-decenoic acid, 1-undecenoic acid, 2-undecenoic acid, 3-undecenoic acid, 1-dodecenoic acid, 2-dodecenoic acid, 3-dodecenoic acid, 1-tridecenoic acid, 2-tridecenoic acid, 3-tridecenoic acid, 1-tetradecenoic acid, 2-tetradecenoic acid, and 3-tetradecenoic acid.

In some embodiments, the medium comprising the carboxylic acid substrate comprises a buffer. Examples of buffers include, without limitation, phosphate buffer, Tris buffer, MOPS buffer, HEPES buffer, citrate buffer, acetate buffer, malate buffer, MES buffer, histidine buffer, PIPES buffer, bis-tris buffer, and ethanolamine buffer.

In some embodiments, the medium comprising the carboxylic acid substrate comprises a surfactant to help dispersion of the substrate. Non-limiting examples of surfactants include polysorbate 20 (TWEEN® 20), polyoxyethylenesorbitan monopalmitate (TWEEN® 40), 4-(1,1,3,3-Tetramethylbutyl)phenyl-polyethylene glycol (TRITON™ X-100), sodium dodecyl sulfate (SDS), ethyl trimethylammonium bromide (ETMAB), lauryl trimethyl ammonium bromide (LTAB), and lauryl trimethylammonium chloride (LTAC).

A medium comprising the carboxylic acid substrate may comprise any concentration of the carboxylic acid substrate. In some embodiments, the medium comprising the carboxylic acid substrate can include 0.5 g/L to 100 g/L of the carboxylic acid substrate, e.g., 1 g/L to 10 g/L of the carboxylic acid substrate. In some embodiments, the medium comprising the carboxylic acid substrate can include 0.5 g/L, 1 g/L, 2 g/L, 3 g/L, 4 g/L, 5 g/L, 6 g/L, 7 g/L, 8 g/L, 9 g/L, 10 g/L, 20 g/L, 30 g/L, 40 g/L, 50 g/L, 60 g/L, 70 g/L, 80 g/L, 90 g/L or 100 g/L of the carboxylic acid substrate.

Lactones

According to methods described herein, the carboxylic acid substrate is converted to a 4-hydroxy carboxylic acid in the presence of the CYP450 protein described herein. Upon acidification, the 4-hydroxy carboxylic acid can be converted to the corresponding gamma lactone. Acidification can be carried out with an acid such as hydrochloric acid, acetic acid, and the like. According to the present disclosure, the methods provided herein can convert 4-hydroxy carboxylic acids into various γ-lactones, including without limitation, γ-hexalactone, γ-hexenolactone, γ-heptalactone, γ-heptenolactone, γ-octalactone, γ-octenolactone, γ-nonalactone, γ-nonenolactone, γ-decalactone, γ-decacenolactone, γ-undecalactone, γ-undecenolactone, γ-dodecalactone, γ-dodecenolactone, γ-tridecalactone, γ-tridecenolactone, γ-tetradecalactone, and γ-tetradecenolactone.

The gamma lactones produced according to methods described herein can be isolated or purified from the cell culture using any method known in the art. For example, the gamma lactones can be isolated or purified from the cell culture by solvent extraction, distillation, chromatographic separation, high pressure liquid chromatography and the like. The isolated or purified lactones can be incorporated into a product, e.g., a food, a beverage, a perfume or a cosmetic product.

Cellular Systems

As referred herein, a cellular system according to the present methods can include any cell or cells that provide for expression of the CYP450 proteins described herein. Such cellular system can include, but are not limited to, bacterial cells, yeast cells, plant cells, and animal cells. In some embodiments, the cellular system comprises bacterial cells, yeast cells, or a combination thereof. In some embodiments, the cellular system comprises prokaryotic cells, eukaryotic cells, and combinations thereof. In some embodiments, the cellular system comprises in vitro expression of proteins based on cellular components, such as ribosomes.

Bacterial cells of the present disclosure include, without limitation, *Escherichia* spp., *Streptomyces* spp., *Zymomonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp.,

*Chromobacterium* spp., *Sinorhizobium* spp., *Saccharopolyspora* spp., *Agrobacterium* spp., *Pantoea* spp., and *Vibrio natriegens*.

Yeast cells of the present disclosure include, without limitation, engineered *Saccharomyces* spp., *Schizosaccharomyces, Hansenula, Candida, Kluyveromyces, Yarrowia, Candida boidinii*, and *Pichia*. According to the current disclosure, a yeast as claimed herein are eukaryotic, single-celled microorganisms classified as members of the fungus kingdom. Yeasts are unicellular organisms which evolved from multicellular ancestors but with some species useful for the current disclosure being those that have the ability to develop multicellular characteristics by forming strings of connected budding cells known as pseudo hyphae or false hyphae.

In some embodiments, cell pellets are harvested from the cellular system expressing CYP450. In some embodiments, the cell pellets may be resuspended at various concentrations. In some embodiments, the cell pellets are resuspended at a concentration of 1 g/L to 250 g/L. In some embodiments, the cell pellets harvested from the cellular system are resuspended at a concentration of 1 g/L, 10 g/L, 25 g/L, 50 g/L, 75 g/L, 100 g/L, 125 g/L, 150 g/L, 175 g/L, 200 g/L, 225 g/L, or 250 g/L.

Cell Culture

A cell culture refers to any cell or cells that are in a culture. Culturing or incubating is the process in which cells are grown under controlled conditions, typically outside of their natural environment. For example, cells, such as yeast cells, may be grown as a cell suspension in liquid nutrient broth. A cell culture includes, but is not limited to, a bacterial cell culture, a yeast cell culture, a plant cell culture, and an animal cell culture. In some embodiments, the cell culture comprises bacterial cells, yeast cells, or a combination thereof.

A bacterial cell culture of the present disclosure comprises bacterial cells including, but not limited to, *Escherichia* spp., *Streptomyces* spp., *Zymomonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., *Pantoea* spp., and *Vibrio natriegens*.

A yeast cell culture of the present disclosure comprises yeast cells including, but not limited to *Saccharomyces* spp., *Schizosaccharomyces, Hansenula, Candida, Kluyveromyces, Yarrowia, Candida boidinii*, and *Pichia*.

In some embodiments, a cell culture as described herein can be an aqueous medium including one or more nutrient substances as known in the art. Such liquid medium can include one or more carbon sources, nitrogen sources, inorganic salts, and/or growth factors. Suitable carbon sources can include glucose, fructose, xylose, sucrose, maltose, lactose, mannitol, sorbitol, glycerol, and corn syrup. Examples of suitable nitrogen sources can include organic and inorganic nitrogen-containing substances such as peptone, corn steep liquor, mean extract, yeast extract, casein, urea, amino acids, ammonium salts, nitrates and mixtures thereof. Examples of inorganic salts can include phosphates, sulfates, magnesium, sodium, calcium, and potassium salts. The liquid medium also can include one or more vitamins and/or minerals.

In some embodiments, cells are cultured at a temperature of 16° C. to 40° C. For example, cells may be cultured at a temperature of 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C. or 40° C.

In some embodiments, cells are cultured at a pH range from about 3 to about 9, preferably in the range of from about 4 to about 8. The pH can be regulated by the addition of an inorganic or organic acid or base such as hydrochloric acid, acetic acid, sodium hydroxide, calcium carbonate, ammonia, or by the addition of a buffer such as phosphate, phthalate or Tris®.

In some embodiments, cells are cultured for a period of time of 0.5 hours to 96 hours, or more. For example, cells may be cultured for a period of time of 12, 18, 24, 30, 36, 42, 48, 54, 60, 66, or 72 hours. Typically, cells, such as bacterial cells, are cultured for a period of time of 12 to 24 hours. In some embodiments, cells are cultured for 12 to 24 hours at a temperature of 37° C. In some embodiments, cells are cultured for 12 to 24 hours at a temperature of 16° C.

In some embodiments, cells are cultured to a density of $1 \times 10^8$ ($OD_{600} < 1$) to $2 \times 10^{11}$ (OD~200) viable cells/ml cell culture medium. In some embodiments, cells are cultured to a density of $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, or $2 \times 10^{11}$ viable cells/ml. (Conversion factor: OD $1 = 8 \times 10^8$ cells/ml).

Synthetic Biology

Standard recombinant DNA and molecular cloning techniques used here are well known in the art and are described, for example, by Sambrook, J., Fritsch, E. F. and Maniatis, T. MOLECULAR CLONING: A LABORATORY MANUAL, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. EXPERIMENTS WITH GENE FUSIONS; Cold Spring Harbor Laboratory: Cold Spring Harbor, N.Y., 1984; and Ausubel, F. M. et al., IN CURRENT PROTOCOLS IN MOLECULAR BIOLOGY, published by GREENE PUBLISHING AND WILEY-INTERSCIENCE, 1987; the entirety of each of which is hereby incorporated herein by reference.

Bacterial Production Systems

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

Persons of ordinary skill in the art will be aware of the molecular biology techniques available for the preparation of expression vectors. The polynucleotide used for incorporation into the expression vector of the subject technology, as described herein, can be prepared by routine techniques such as polymerase chain reaction (PCR).

A number of molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or E. coli DNA polymerase I, enzymes that remove protruding, 3'-single-stranded termini with their 3'-5'-exonucleolytic activities and fill-in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, NUCL. ACID. RES. 18 6069-74, (1990), Haun, et al, BIOTECHNIQUES 13, 515-18 (1992), which is incorporated herein by reference to the extent it is consistent herewith).

In an embodiment, in order to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared by the use of PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector, In some embodiments, the transformed cell can be a bacterial cell, a yeast cell, an algal cell, a fungal cell, a plant cell, an insect cell or an animal cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a petunia plant cell.

Microbial host cell expression systems and expression vectors containing regulatory sequences that direct high-level expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYCI, HIS3, GALI, GALIO, ADHI, PGK, PH05, GAPDH, ADCI, TRPI, URA3, LEU2, ENO, TPI (useful for expression in Saccharomyces); AOXI (useful for expression in Pichia); and lac, trp, JPL, IPR, T7, tac, and trc (useful for expression in Escherichia coli).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns in order to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with an expression vector of the subject technology should be capable of promoting the expression of the vector. High level plant promoters that may be used in the subject technology include the promoter of the small subunit (s) of the ribulose-1,5-bisphosphate carboxylase for example from soybean (Berry-Lowe et al., J. MOLECULAR AND APP. GEN., 1:483-98 (1982), the entirety of which is hereby incorporated herein to the extent it is consistent herewith), and the promoter of the chlorophyll binding protein. These two promoters are known to be light-induced in plant cells (see, for example, GENETIC ENGINEERING OF PLANTS, AN AGRICULTURAL PERSPECTIVE, A. Cashmore, Plenum, N.Y. (1983), pages 29-38; Coruzzi, G. et al., THE JOURNAL OF BIOLOGICAL CHEMISTRY, 258: 1399 (1983), and Dunsmuir, P. et al., JOURNAL OF MOLECULAR AND APPLIED GENETICS, 2:285 (1983), each of which is hereby incorporated herein by reference to the extent they are consistent herewith).

Analysis of Sequence Similarity Using Identity Scoring

As used herein, "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this disclosure "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, JOURNAL OF MOLECULAR BIOLOGY 48:443-53, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL. 215:403-10 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the disclosure is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity of the Cytochrome P450 genes of the current disclosure are capable of directing the production of a variety of γ- and delta-lactones, Such polynucleotide molecules can have a substantial percent sequence identity to the polynucleotide sequences provided herein and are encompassed within the scope of this disclosure.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

Explanation of Terms Used Herein

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "complementary" is to be given its ordinary and customary meaning to a person of ordinary skill in the art and is used without limitation to describe the relationship between nucleotide bases that are capable to hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences.

The terms "nucleic acid" and "nucleotide" are to be given their respective ordinary and customary meanings to a person of ordinary skill in the art and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

"Coding sequence" is to be given its ordinary and customary meaning to a person of ordinary skill in the art, and is used without limitation to refer to a DNA sequence that encodes for a specific amino acid sequence.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing the desired product.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are to be given their respective ordinary and customary meanings to a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full-length polypeptide or protein, and has substantially the same biological activity, or carries out substantially the same function as the full-length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

"Percent (%) amino acid sequence identity" with respect to the variant polypeptide sequences of the subject technology refers to the percentage of amino acid residues in a candidate sequence that are identical with the amino acid residues of a reference polypeptide, after aligning the sequences and introducing gaps, if necessary, to achieve the maximum percent sequence identity, and not considering any conservative substitutions as part of the sequence identity.

Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, the % amino acid sequence identity may be determined using the sequence comparison program NCBI-BLAST2. The NCBI-BLAST2 sequence comparison program may be downloaded from ncbi.nlm.nih.gov. NCBI BLAST2 uses several search parameters, wherein all of those search parameters are set to default values including, for example, unmask yes, strand=all, expected occurrences 10, minimum low complexity length=15/5, multi-pass e-value=0.01, constant for multi-pass=25, dropoff for final gapped alignment=25 and scoring matrix=BLOSUM62. In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In this sense, techniques for determining amino acid sequence "similarity" are well known in the art. In general, "similarity" refers to the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known by those skilled in the art.

An amino acid position "corresponding to" a reference position refers to a position that aligns with a reference sequence, as identified by aligning the amino acid sequences. Such alignments can be done by hand or by using well-known sequence alignment programs such as ClustalW2, Blast 2, etc.

Unless specified otherwise, the percent identity of two polypeptide or polynucleotide sequences refers to the percentage of identical amino acid residues or nucleotides across the entire length of the shorter of the two sequences.

The term "homologous" in all its grammatical forms and spelling variations refers to the relationship between polynucleotides or polypeptides that possess a "common evolutionary origin," including polynucleotides or polypeptides from super families and homologous polynucleotides or proteins from different species (Reeck et al., CELL 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 900 at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art, and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of reasonable skill in the field, and is used without limitation to refer to the transfer of a polynucleotide into a target cell for further expression by that cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "transformed," "transgenic," and "recombinant," when used herein in connection with host cells, are to be given their respective ordinary and customary meanings to a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

EXAMPLES

Example 1: Identifying Candidate Genes for Fungal Cytochrome P450 Enzymes with Fatty Acid 4-Hydroxylase Activity Cytochrome P450 (CYP) enzymes can catalyze the oxidation of a wide variety of organic substrates (including fatty acids) to generate various hydroxylated compounds (including hydroxy fatty acids). However, the position of the carbon atom at which the hydroxylation takes place along the hydrocarbon backbone can be critical. For example, among various P450s, bacterial and fungal P450 BM3 enzymes have been reported to catalyze the formation of $\omega$-1 to $\omega$-3 hydroxy fatty acids. See e.g., Miura, Y. and Fulco, A. J., "$\omega$-1, $\omega$-2 and $\omega$-3 Hydroxylation of Long-Chain Fatty Acids, Amides and Alcohols by a Soluble Enzyme System from *Bacillus megatyerium,*" *Biochimica et Biophysica Acta—Lipids and Lipid Metabolism*, 388(3): 305-317 (1975); and Kitazume, T. et al., "*Fusarium oxysporum* Fatty-acid Subterminal Hydroxylase (CYP505) Is a Membrane-bound Eukaryotic Counterpart of *Bacillus megaterium* Cytochrome P450BM3,*" J. Bio. Chem.,* 275: 39734-39740 (2000).

Referring to FIG. 1, an efficient synthetic pathway from various fatty acids to gamma-lactones involve the hydroxylation of the carbon atom positioned gamma to the carbonyl carbon of the fatty acid substrate, thereby generating a 4-hydroxy fatty acid (4-hydroxylase route). Subsequently, the 4-hydroxy fatty acid can be converted into a gamma-lactone under acidic conditions.

It has been reported that some filamentous fungi such as *Mucor circinelloides, Aspergillus oryzae,* and *Mortierella isabellina* can make various gamma- or delta-lactones from the corresponding carboxylic acids. See U.S. Pat. Nos. 5,032,513 and 7,863,023. Nevertheless, the molecular mechanisms for their bioconversion activities are largely unknown. In addition, the complex morphology of such filamentous fungi makes the scale-up of these processes a big challenge.

To the inventors' knowledge, previous to the current invention, no specific fatty acid 4-hydroxylase genes or enzymes have been identified. After performing rigorous high-throughput screening of large libraries of candidate genes for fungal cytochrome P450 (CYP, P450, or CYP450) enzymes with fatty acid 4-hydroxylase activity, the inventors identified the following candidate genes: a cytochrome P450 monooxygenase gene (GenBank: GAN03094.1) from *Mucor ambiguus,* the amino acid sequence of said *Mucor ambiguus* CYP is provided as SEQ ID NO: 1; a cytochrome P450 monooxygenase gene (GenBank: ORX85448.1) from *Basidiobolus meristosporus,* the amino acid sequence of said *Basidiobolus meristosporus* CYP is provided as SEQ ID NO: 3; and a cytochrome P450 monooxygenase gene (GenBank: ORX85448.1) from *Umbelopsis isabellina,* the amino acid sequence of said *Umbelopsis isabellina* CYP is provided as SEQ ID NO: 5.

Example 2: Generation of High Yield Strains and Overexpression of Cytochrome P450 for Producing Gamma-Lactones To facilitate protein expression in *E. coli,* each of the candidate genes was codon-optimized for *E. coli* genome and synthesized by Gene Universal Inc. (Newark, Del.).

The codon-optimized *Mucor ambiguus* P450 gene was cloned into a pET17b vector (AMP+, Novagen) through HindIII and XhoI sites. The construct was transformed into BL21(DE3) cells for expression. In a typical experiment, an overnight culture was used to inoculate liquid LB medium (2%) containing 100 mg/L of carbenicillin. The culture was first grown at 37° C. to an OD600 of 0.6 and cooled down to 25° C. Then 1 mM of IPTG was added to induce protein expression. After 3 hours of incubation at 25° C., the fatty acid substrate was added at 1 g/L for γ-lactone production.

Each of the codon-optimized *Basidiobolus meristosporus* P450 and *Umbelopsis isabellina* P450 genes was cloned into pET-32a-(+) vector (AMP+, Novagen) through HindIII and XhoI sites. The construct was transformed into BL21(DE3) cells for expression. In a typical experiment, an overnight culture was used to inoculate liquid LB medium (2%) containing 100 mg/L of carbenicillin. The culture was first grown at 37° C. to an OD600 of 0.8 and cooled down to 16° C. Then 1 mM of IPTG was added to induce protein expression. After 5 h of incubation at 16° C., the temperature was raised to 30° C. and the fatty acid substrate was added at 1 g/L for γ-lactone production.

Example 3: Analysis of Gamma-Lactone Production

To analyze γ-lactone production, 0.5 ml of the *E. coli* culture described in Example 2 was taken and acidified with 10 μl of 2N HCl, then extracted with 0.5 ml of ethyl acetate with shaking at room temperature for 60 min. After centrifugation at 14,000 rpm for 15 min, the ethyl acetate phase was used for GC/MS or GC/FID analysis.

GC/MS analysis was conducted on Shimadzu GC-2010 system coupled with GCMS-QP2010S detector. The analytical column is SHRXI-5MS (thickness 0.25 μm; length 30 m; diameter 0.25 mm) and the injection temperature is 265° C. under split mode. The temperature gradient is 0-3 min 80° C.; 3-8.7 min 120° C. to 263° C., a gradient of 25; 8.7-10.7 min, 263° C.

GC/FID analysis was conducted on Shimadzu GC-2014 system. The analytical column is Restek RXi-5 ms (thickness 0.25 μm; length 30 m; diameter 0.25 mm) and the injection temperature is 240° C. under split mode. The temperature gradient is 0-3 min, 100° C.; 3-9 min 100° C.-280° C., a gradient of 30; 9-12 min, 280° C.

Example 4: Gamma-Lactone Production Using High Yield Strains Overexpressing *Mucor ambiguus* P450

The procedures described in Example 2 were performed using an *E. coli* culture overexpressing *Mucor ambiguus* P450. Specifically, samples of the *E. coli* culture were taken and acidified 2 days or 16 h after adding the fatty acid substrate. FIGS. 2a-2h show the production of various gamma-lactones from the corresponding carboxylic acid: (a) γ-heptalactone (GC7) from enanthic acid (heptanoic acid, C7), (b) γ-octalactone (GC8) from caprylic acid (octanoic acid, C8), (c) γ-nonalactone (GC9) from pelargonic acid (nonanoic acid, C9), (d) γ-decalactone (GC10) from capric acid (decanoic acid, C10), (e) γ-undecalactone (GC11) from undecylic acid (undecanoic acid, C11), (f) γ-dodecalactone (GC12) from lauric acid (dodecanoic acid, C12), (g) γ-tridecalactone (GC13) from tridecylic acid (tridecanoic acid, C13), and (h) γ-tetradecalactone (GC14) from myristic acid (tetradecanoic acid, C14).

As shown in FIG. 2a to FIG. 2h, GC7-GC14 γ-lactones were effectively produced from the corresponding C7-C14 carboxylic acids in a heterologous system that overexpressed *Mucor ambiguus* cytochrome P450 (SEQ ID NO: 1). Notably, the GC7 to GC12 peaks match the corresponding standards from Sigma-Aldrich (St Louis, Mo.) in terms of both retention times and mass spectra. The standards for γ-tridecalactone (GC13) and γ-tetradecalactone (GC14) are not commercially available. Nevertheless, it was noted that the putative GC13 and GC14 peaks have retention times longer than that of GC12.

Example 5: Gamma-Lactone Production Using High Yield Strains Overexpressing *Basidiobolus meristosporus* P450

Figure 3:
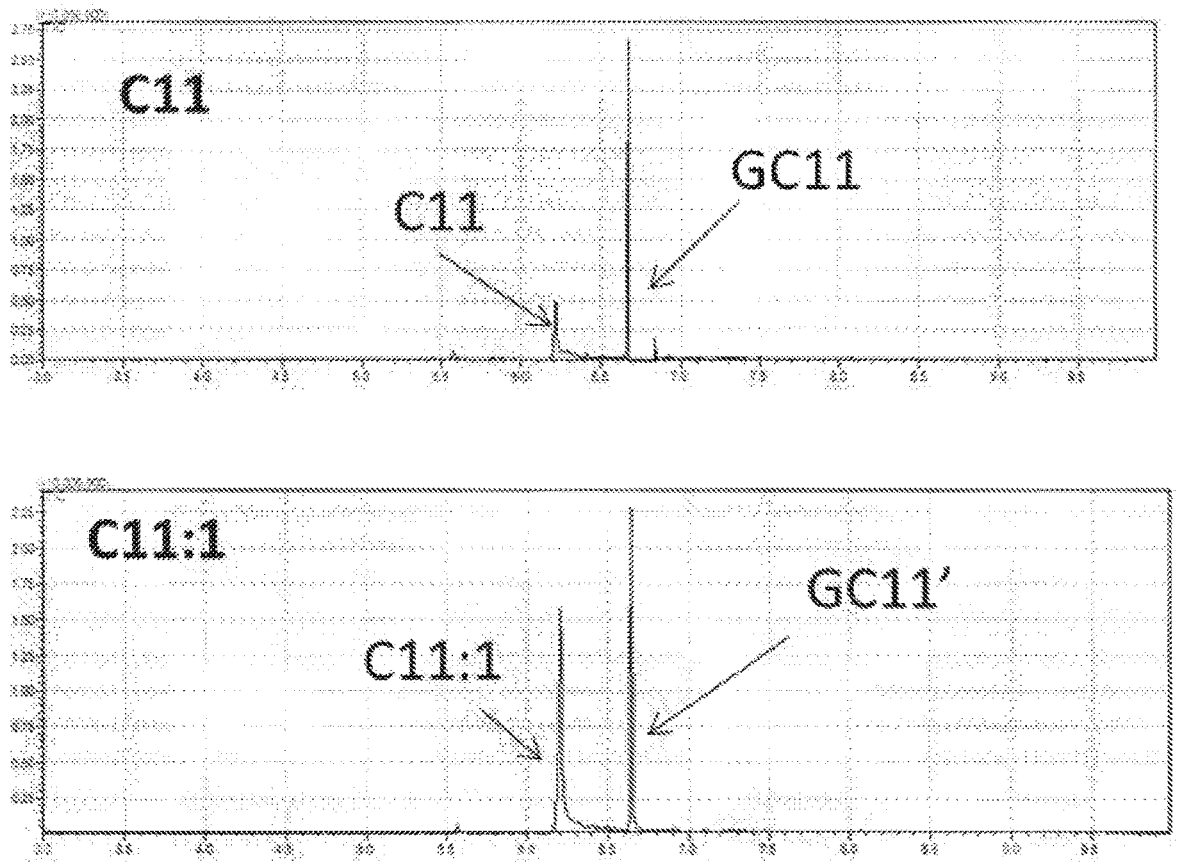
FIG. 3 shows GC/MS spectra confirming γ-lactone production using an *E. coli* culture transformed to overexpress *Basidiobolus meristosporus* P450. Specifically, the top panel shows the production of γ-undecalactone (GC11) from undecylic acid (undecanoic acid, C11). The bottom panel shows the production of γ-undecenolactone (GC11') from undecylenic acid (undecenoic acid, C11:1).
Figure 4A:
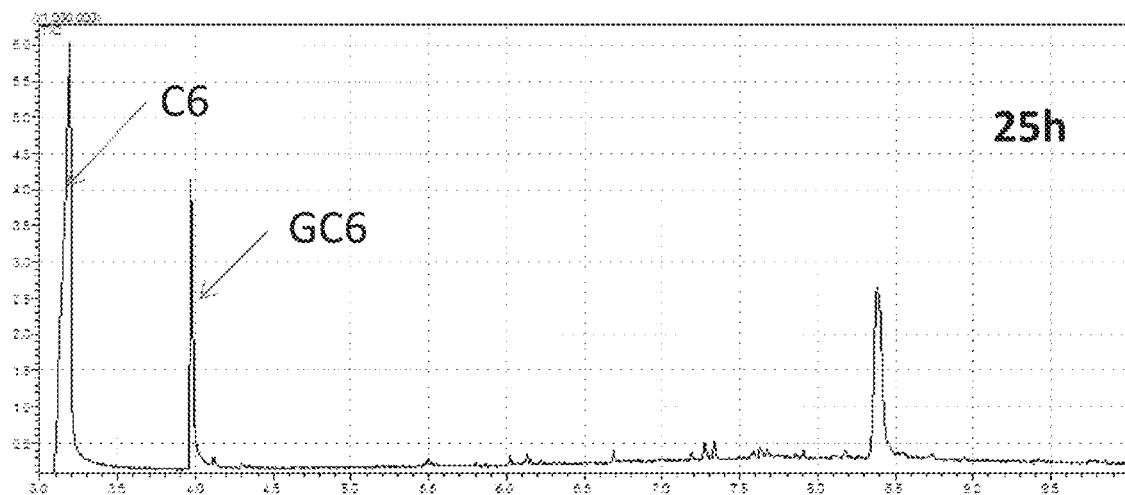
FIGS. 4a-4g show GC/MS spectra confirming production of various γ-lactones using an *E. coli* culture transformed to overexpress *Umbelopsis isabellina* P450. Specifically.
Figure 4B:
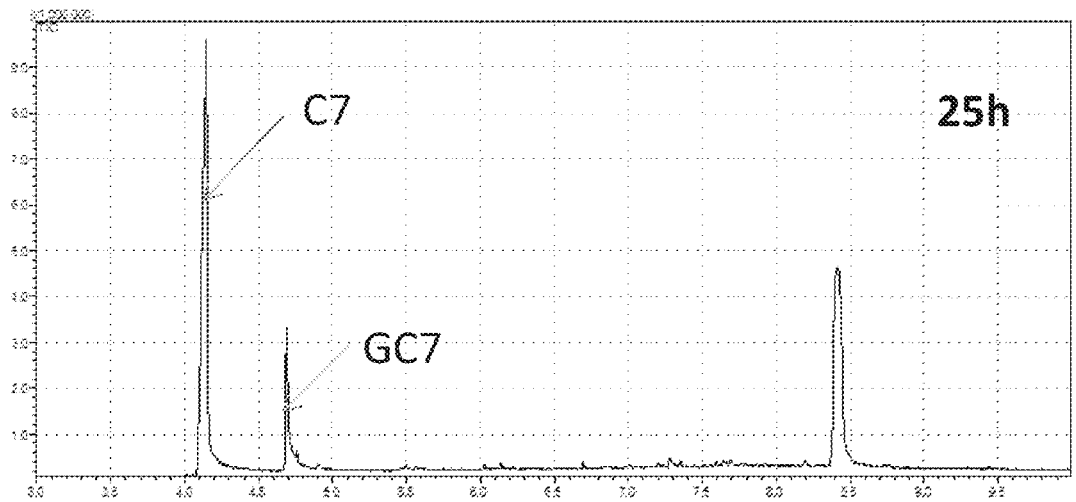
Figure 4C:
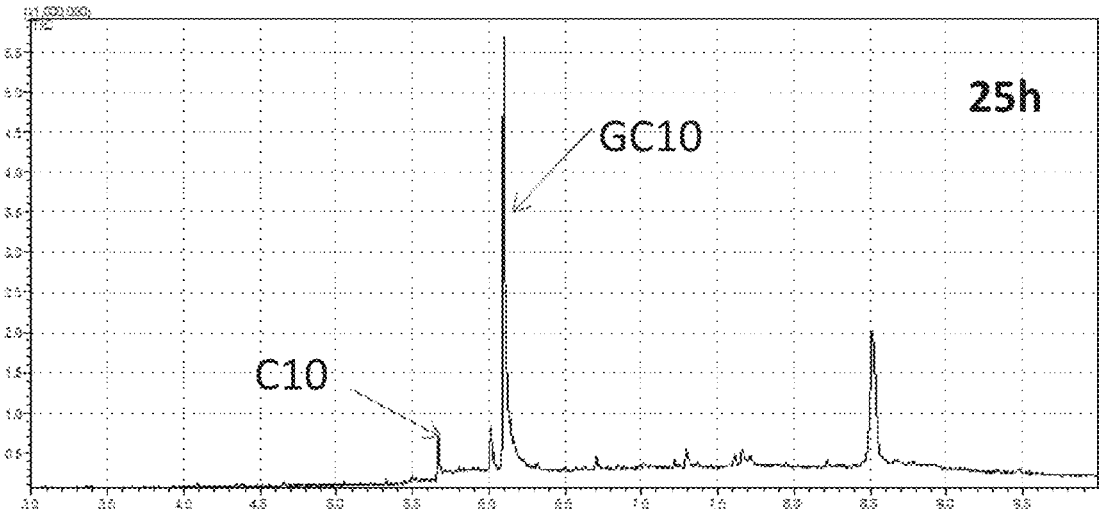
Figure 4D:
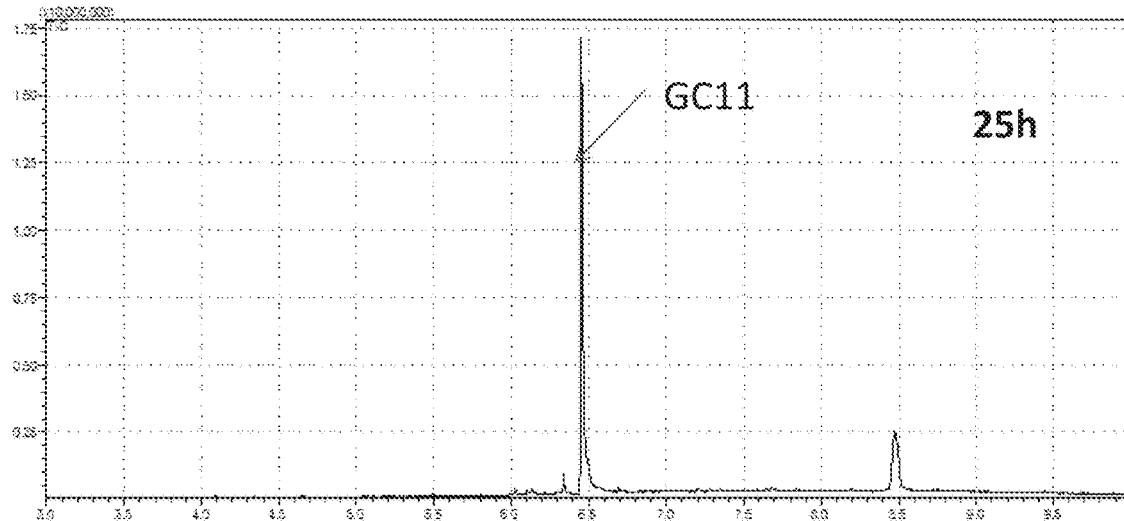
Figure 4E:
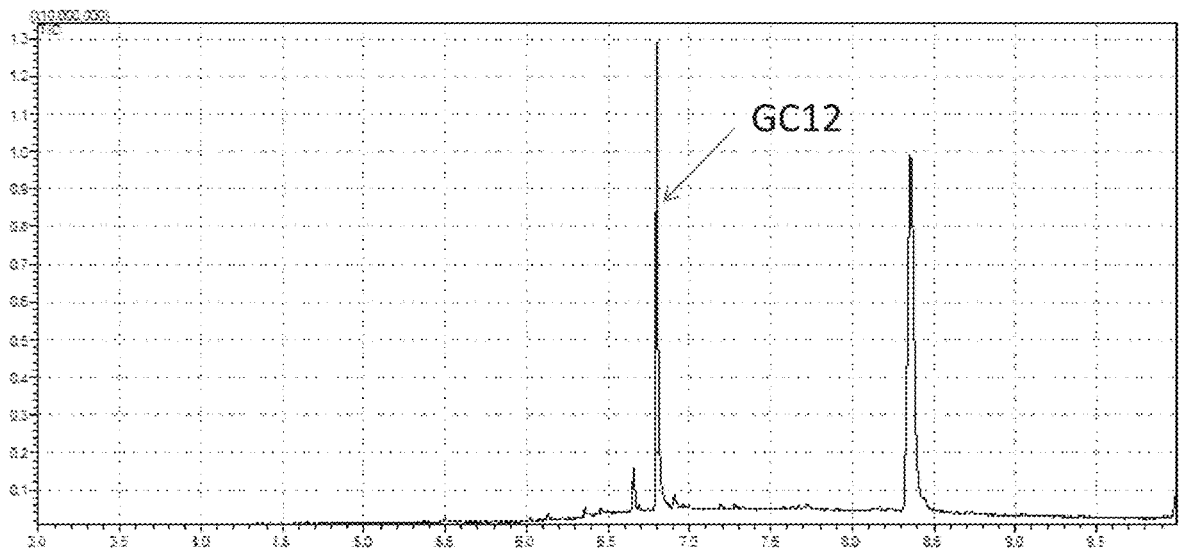
Figure 4F:
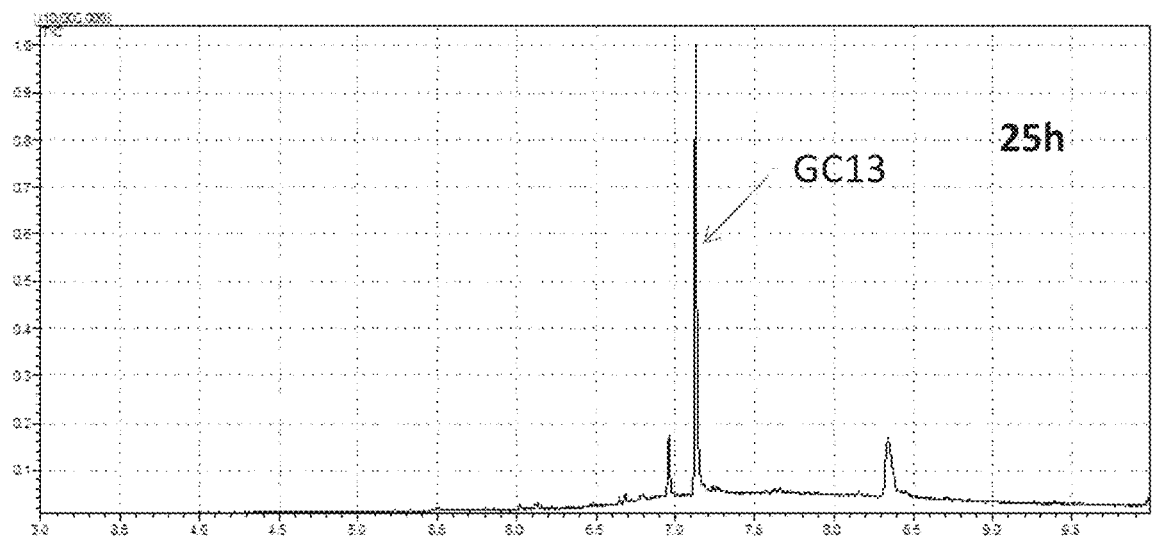
Figure 4G:
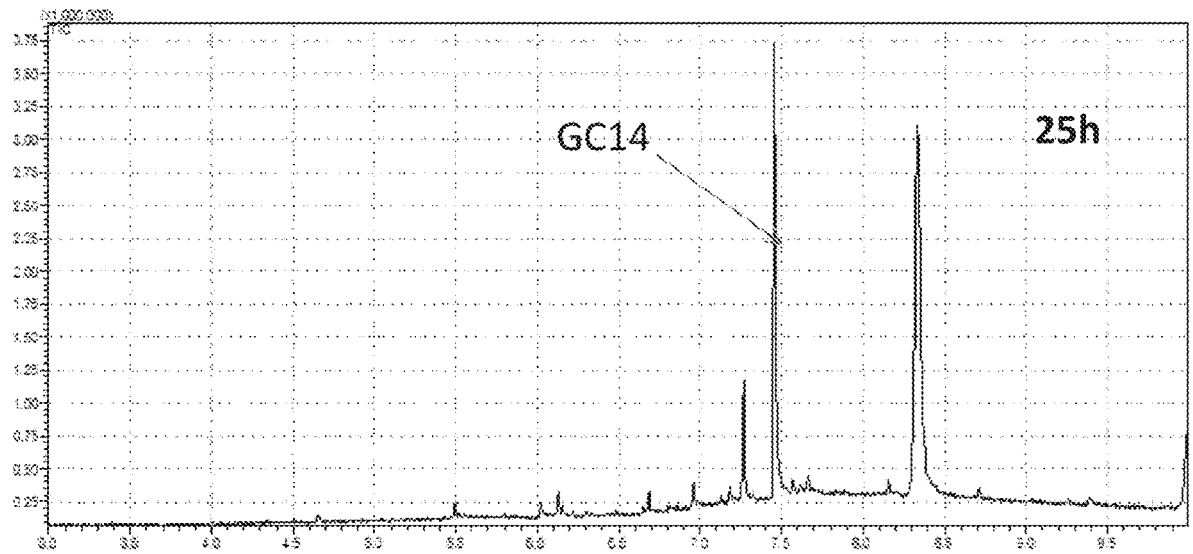

The procedures described in Example 2 were performed using an *E. coli* culture overexpressing *Basidiobolus meristosporus* P450. Specifically, samples of the *E. coli* culture were taken and acidified 17 hours after adding the fatty acid substrate. FIG. 3 shows the production of various gamma-lactones from the corresponding carboxylic acid: (a) γ-undecalactone (GC11) from undecylic acid (undecanoic acid, C11), and (b) γ-undecenolactone (GC11') from undecylenic acid (undecenoic acid, C11:1).

As shown in FIG. 3, GC11 and GC11' γ-lactones were effectively produced from the corresponding C11 and C11:1 carboxylic acids in a heterologous system that overexpressed *Basidiobolus meristosporus* cytochrome P450 (SEQ ID NO: 3). Notably, the C11, GC11 and C11:1 peaks match the corresponding standards from Sigma-Aldrich (St Louis, Mo.) in terms of both retention times and mass spectra. The standard for GC11' is not commercially available. Nevertheless, it was noted that the putative GC11' peak shows a retention time similar to that of GC11.

Under the reaction conditions described, about 69 mg/L of GC11 and about 18 mg/L of GC11' were produced 17 hours after adding 1 g/L of C11 or C11:1 to the *E. coli* growing cell cultures, respectively.

In addition to growing cells, resting cells were also investigated for their potential use in the bioconversion of fatty acids into gamma-lactones. In this experiment, an overnight culture was used to inoculate liquid SOC medium (3%) containing 100 mg/L of carbenicillin. The culture was first grown at 37° C. to an OD600 of 0.8 and cooled down to 16° C. Then, 1 mM of IPTG was added to induce protein expression. After 16 h of incubation at 16° C., the culture was harvested and cell pellets were collected by centrifugation and stored at −80° C. until use. In a typical bioconversion experiment, the frozen cells were re-suspended in 100 mM K-Pi buffer, pH7 at a cell concentration of 100 g/L fresh weight. Then, 1 g/L of C11 or C11:1 was added together with 0.1% of Tween 40 and 10 mM of NADPH. Subsequently, the mixture was incubated at 30° C. with shaking at 250 rpm. Samples were taken 3 h later. The titers for GC11 and GC11' were 419 mg/L and 185 mg/L, respectively.

Example 6: Gamma-Lactone Production Using High Yield Strains Overexpressing *Umbelopsis isabellina* P450

The procedures described in Example 2 were performed using an *E. coli* culture overexpressing *Umbelopsis isabellina* P450. Specifically, samples of the *E. coli* culture were taken and acidified 25 hours after adding the fatty acid substrate. FIGS. 4a-4g show the production of various gamma-lactones from the corresponding carboxylic acid: (a) γ-undecalactone (GC11) from undecylic acid (undecanoic acid, C11), and (b) γ-undecenolactone (GC11') from undecylenic acid (undecenoic acid, C11:1) retention time min.

FIG. 4 shows the production of various gamma-lactones from the corresponding carboxylic acid: (a) γ-hexalactone (GC6) from hexanoic acid (C6), (b) γ-heptalactone (GC7) from enanthic acid (heptanoic acid, C7), (c) γ-decalactone (GC10) from capric acid (decanoic acid, C10), (d) γ-undecalactone (GC11) from undecylic acid (undecanoic acid, C11), (e) γ-dodecalactone (GC12) from lauric acid (dodecanoic acid, C12), (f) γ-tridecalactone (GC13) from tridecylic acid (tridecanoic acid, C13), and (g) γ-tetradecalactone (GC14) from myristic acid (tetradecanoic acid, C14).

As shown in FIG. 4a to FIG. 4g, GC6, GC7, GC10, GC11, GC12, GC13, and GC14 γ-lactones were effectively produced from the corresponding C6, C7, C10, C11, C12, C13, and C14 carboxylic acids in a heterologous system that overexpressed *Umbelopsis isabellina* cytochrome P450 (SEQ ID NO: 5). Notably, the GC6, GC7, GC10, GC11 and GC12 peaks match the corresponding standards from Sigma-Aldrich (St Louis, Mo.) in terms of both retention times and mass spectra. The standards for γ-tridecalactone (GC13) and γ-tetradecalactone (GC14) are not commercially available. Nevertheless, it was noted that the putative GC13 and GC14 peaks have retention times longer than that of GC12.

Under the reaction conditions described, about 42 mg/L of GC6 was produced 25 hours after adding 1 g/L of C6 to the *E. coli* growing cell culture.

In addition to growing cells, resting cells were also investigated for their potential use in the bioconversion of fatty acids into gamma-lactones. In this experiment, an overnight culture was used to inoculate liquid SOC medium (3%) containing 100 mg/L of carbenicillin. The culture was first grown at 37° C. to an OD600 of 0.8 and cooled down to 16° C. Then, 1 mM of IPTG was added to induce protein expression. After 16 h of incubation at 16° C., the culture was harvested and cell pellets were collected by centrifugation and stored at −80° C. until use. In a typical bioconversion experiment, the frozen cells were re-suspended in 100 mM K-Pi buffer, pH7 at a cell concentration of 100 g/L fresh weight. Then, 1 g/L of C6 was added and the mixture was incubated at 30° C. with shaking at 250 rpm. Samples were taken 3 h later. The titer for GC6 was 198 mg/L.

```
Sequences of Interest:
Mucor ambikuus cytochrome P450
Amino acid sequence of the GAN03094.1 gene (SEQ ID NO: 1):
MTKYAHDQ1PGPEPHYLLGNVPDIFPDSLGNLIKLHDKYGPIVHLSMGGHELLSVDDPA

VLETICEDNEYFTKEIESVYSDLAILNGRGLVTTSTADPDWQLGHKLIMNAFSARAMKA

YHYKMGESISELCEIMDSFAKSGEDFDVSRWFIALALESIGKIGFDYDFDLLKDPNAPRH

PFTVALAYVQSMIMKRASTLSWLKWYQTTTNVRFHRDLQTLRGTVEEVLKDRREHPHT

EADQSDLLDFMIKAESKEGEKLNDSLIRDNIITFLSAGHNTTSAFLSWTMLELCKHPEVV

ENIKQEIANCGIKAGEVPTPEQVKECKYLDLVIKESLRIHPPITSILKYCKKDATVKASNG

DEYDIKAGQLLQVNINALHHNPKVWEDPDVFNPDRFSGDTDNLPNTAWLTFSTGPRACI

GRQFALQEGKLALVMILSRFHFKMDDPSQKIGYAVVVSTKPVGFFAKIESSQLPEPTEEI

VVTKRRESKAVPQEKVKPAEFPLPPVTFLFGTQTNTSEEYARKLSGQAKEMGFKEVTVQ
```

-continued

DLDDWKLVKGEAIAKAQHDADAPSSEDDVKVSELVVVVTATYNGFPPDDANEFAKWL

DERTKDSEATKNNMLSGMLYAVFGCGNRDWTSTFQKFPKKVDSGFELLGGERLLPAGE

GDASDDIDGDFSLWSASFWTALMQRYGQSSSGKNADIMSNNGPAADPSQDFTLEFINIV

KEKVKTEQAALNCNQLETVATIVENRELQHTEKSHRSTRHIQVQFDKSVDGKPLYEAGD

HLEVVPVNEDRLVEIIATNLGLVLDSVFEVKDLDIKNLSPRSVAANIKGPCTIRNALKYY

ADLTGPPTRFSLSILSKQLKDSRPDIAERLQKALQPGKETERLKEFLASHRTLIDIIQAFKI

KELNFKEFISSVNCIVPRKYSISSGPLEHPFDPSISVGVVDTVGGPDGNTHYFGLASGYLS

HQEPGTKINAQIKACKSTFRLPDDPSTPVIFIAAGTGFSPFRGFLQERHAKGLKSSKKNSN

GESSECYMFFGCRHPDQDFIYKEEFDAYLEDGTITELYTTFSRSGEVVKYVQHALLKHA

NLLYKLMEESNAKVYICGSAGSMAKDVKRTWERLLVQMSGVSESEAAEQIQAWVDEG

KYNEDVWGT

Nucleotide sequence of GAN03094.1, codon-optimized for
E. coli genome (SEQ ID NO: 2):
ATGACCAAATATGCCCATGATCAGATTCCGGGTCCTGAACCGCATTATCTGCTGGGT

AATGTTCCGGATATTTTTCCGGATAGCCTGGGCAATCTGATTAAACTGCATGATAAA

TATGGTCCGATTGTGCATCTGAGCATGGGTGGTCATGAACTGCTGAGCGTTGATGAT

CCGGCAGTTCTGGAAACCATTTGTGAAGATAATGAATATTTCACCAAAGAAATCGA

AAGCGTGTATAGCGATCTGGCAATTCTGAATGGTCGTGGTCTGGTTACCACCAGTAC

CGCAGATCCGGATTGGCAGCTGGGTCATAAACTGATTATGAATGCATTTAGCGCACG

TGCCATGAAAGCCTATCACTATAAAATGGGTGAAAGCATTAGCGAACTGTGCGAAA

TTATGGATAGCTTTGCAAAAAGCGGTGAGGATTTTGATGTTAGCCGTTGGTTTATTG

CACTGGCACTGGAAAGCATTGGTAAAATCGGTTTCGATTATGATTTCGACCTGCTGA

AGATCCGAATGCACCGCGTCATCCGTTTACCGTTGCGCTGGCCTATGTTCAGAGTA

TGATCATGAAACGTGCAAGCACCCTGAGCTGGCTGAAATGGTATCAGACCACCACC

AATGTTCGTTTTCATCGTGATCTGCAGACCCTGCGTGGCACCGTTGAAGAAGTTCTG

AAAGACCGTCGTGAACATCCGCATACCGAAGCAGATCAGAGCGATCTGCTGGATTT

TATGATTAAAGCCGAAAGCAAAGAAGGCGAGAAACTGAACGATAGCCTGATTCGTG

ATAACATCATTACCTTTCTGAGCGCAGGTCATAATACCACCTCAGCATTTCTGAGCT

GGACCATGCTGGAACTGTGTAAACATCCGGAAGTTGTCGAAAACATCAAACAAGAA

ATTGCCAACTGCGGTATTAAAGCGGGTGAAGTTCCGACACCGGAACAGGTTAAAGA

ATGTAAATATCTGGACCTGGTGATCAAAGAAAGCCTGCGTATTCATCCGCCTATTAC

CAGCATTCTGAAATACTGTAAAAAAGACGCAACCGTGAAAGCCAGCAATGGTGATG

AATATGATATTAAAGCAGGTCAGCTGCTGCAGGTTAACATTAATGCACTGCATCATA

ACCCGAAAGTTTGGGAAGATCCTGATGTTTTTAACCCGGATCGTTTTAGCGGTGATA

CCGATAATCTGCCGAATACCGCATGGCTGACCTTTAGCACCGGTCCGCGTGCATGTA

TTGGTCGTCAGTTTGCACTGCAAGAAGGTAAACTGGCCCTGGTTATGATTCTGAGCC

GTTTTCATTTCAAAATGGATGATCCGAGCCAGAAAATTGGTTATGCAGTTGTTGTTA

GCACCAAACCGGTTGGTTTTTTTGCCAAAATTGAAAGCAGCCAGCTGCCGGAACCGA

CCGAAGAAATTGTTGTTACCAAACGTCGTGAAAGTAAAGCAGTTCCGCAAGAAAAA

GTTAAACCGGCAGAATTTCCGCTGCCTCCGGTGACCTTTCTGTTTGGCACCCAGACC

AATACCAGCGAAGAATATGCACGTAAACTGAGCGGTCAGGCAAAAGAAATGGGTTT

TAAAGAAGTTACCGTCCAGGATCTGGATGATTGGAAACTGGTTAAAGGTGAAGCAA

```
-continued
TTGCAAAAGCACAGCATGATGCCGATGCACCGAGCAGCGAAGATGATGTTAAAGTG

AGCGAACTGGTTGTTGTTGTGACCGCAACCTATAATGGTTTTCCGCCTGATGATGCA

AACGAATTTGCAAAATGGCTGGATGAACGTACCAAAGATAGCGAAGCAACCAAAAA

TAACATGCTGAGCGGTATGCTGTATGCAGTGTTTGGTTGTGGTAATCGTGATTGGAC

CAGCACCTTTCAGAAATTCCCGAAAAAAGTTGATAGCGGCTTTGAACTGTTAGGTGG

TGAACGTCTGCTGCCAGCCGGTGAAGGTGATGCAAGTGATGATATTGATGGTGATTT

TAGCCTGTGGTCTGCCAGCTTTTGGACCGCACTGATGCAGCGTTATGGTCAGAGCAG

CAGCGGTAAAAATGCAGATATTATGAGCAATAATGGTCCGGCAGCAGATCCGAGTC

AGGATTTTACCCTGGAATTTATCAACATCGTGAAAGAGAAGGTCAAAACCGAACAG

GCAGCACTGAATTGTAATCAGCTGGAAACCGTTGCAACCATTGTTGAAAATCGCGA

ACTGCAGCATACAGAAAAAGCCATCGTAGCACCCGTCATATTCAGGTTCAGTTTGA

TAAAAGCGTGGATGGTAAACCGCTGTATGAAGCCGGTGATCATCTGGAAGTGGTTC

CGGTTAATGAAGATCGTCTGGTTGAAATTATTGCCACCAATCTGGGTTTAGTTCTGG

ATAGCGTTTTTGAGGTGAAAGACCTGGATATTAAGAATCTGAGTCCGCGTAGCGTTG

CAGCAAACATTAAAGGTCCGTGTACCATTCGTAATGCCCTGAAATATTACGCAGATC

TGACCGGTCCTCCGACACGTTTTAGTCTGAGCATTCTGTCAAAACAGCTGAAAGACA

GCCGTCCTGATATTGCAGAACGCCTGCAGAAAGCACTGCAGCCTGGTAAAGAAACC

GAACGTCTGAAAGAATTTCTGGCAAGTCATCGTACCCTGATCGATATTATTCAGGCC

TTCAAAATCAAAGAACTGAACTTCAAAGAGTTTATCAGCAGCGTTAATTGCATCGTT

CCGCGTAAATATAGCATTAGCAGTGGTCCGCTGGAACATCCGTTTGATCCGAGTATT

AGCGTTGGTGTTGTTGATACCGTTGGTGGTCCGGATGGTAATACCCATTATTTTGGTC

TGGCAAGCGGTTATCTGAGCCATCAAGAACCGGGTACAAAAATCAATGCACAGATT

AAAGCATGCAAGAGTACCTTTCGTCTGCCGGATGATCCTAGCACACCGGTTATCTTT

ATTGCAGCAGGCACCGGTTTTAGCCCGTTTCGTGGTTTTCTGCAAGAACGTCATGCA

AAAGGTCTGAAAAGCAGCAAAAAAAACAGCAATGGCGAAAGCAGCGAGTGCTATA

TGTTTTTTGGCTGTCGTCATCCGGATCAGGATTTCATCTATAAAGAAGAATTTGACGC

CTACCTGGAAGATGGCACCATTACAGAACTGTATACCACCTTTAGCCGTAGCGGTGA

AGTTGTTAAATATGTTCAGCACGCACTGCTGAAACATGCAAATCTGCTGTACAAACT

GATGGAAGAAAGCAACGCCAAAGTGTATATTTGTGGTAGCGCAGGTAGCATGGCAA

AAGATGTTAAACGTACCTGGGAGCGCCTGCTGGTTCAGATGAGCGGTGTTAGCGAA

AGCGAAGCAGCAGAGCAGATTCAGGCATGGGTTGATGAAGGCAAATATAACGAAG

ATGTTTGGGGCACCTAA
```

*Basidiobolus meristosporus* cytochrome P450
Amino acid sequence of the ORX85448.1 gene (SEQ ID NO: 3):
```
MSSQSDEIPGPKPHILLGNVQDIIPDTIGNHRRLHDEYGPVMRLYLGGHDFVSICDPEVIQ

SITGEGDFTKEIYSAYEDLAILSGRGLVTTATKDPDWILAHKLLMPAFSARAMKAYHDI

MGKCILDLLKIMESYQECGEAIDMSRWMISLALESIGVIGFGYNFNLLDDKDSERHPFSV

ALNYVQSMIMKRTNSVTWTKWLQTTANVRFRRDLATLRDTVDDVLKQRRLNPPSEDA

RRDLLDFMLAAESKQGEKLDDNLIRDEIITFLSAGHNTTSSFLSWTFFELARNPDVEQKIL

QEIVNAGIKPGEIPSTEQVAKCKYIDMVIKESLRFHSPIPLVIKYCQNDCTIKTSEGKEYEI

KRGQLAQIQISAVHKDPKLWENPNVFDPERFNPEKEADRHPCAWIPFSDGPRACIGRQFS

LQEGKLALIMLLCKFRFRLLDETKEVGYQIIVSLKPVDLIMKVLPAELPSPNAGSDTSSVK
```

-continued

DTVKPQLKPKENEVLEHARFPLPPVTFLYGTQTGTSEEYARKLSGQAKEFGFTDIAVAEL

DDWEVVKNNRIPSNKGQSSPSDEDGTKVSQLAVIVTATYNGYPPDNALKFDSWLTDITK

DQKNQLEGLLYAVFGCGNKQWQSTFQAFPKKVDASIELLGAERLVPAGAGNADQDIDG

DFTNWSASFWAALMQKYGRGASDKDADLMTTSGPVADPSNDFTLEFLPLGGDQAAME

AALGNRNSDPGAQVAILENKELQDVEKSGRSTRHIVVECPPASPGSGKKASYRAGDHLE

IKPYNDDQLVENIAIGFGYVLDSVFQIKDCKITNLSPRSLAANIIGPCTVRNALTYFADLS

GPPTRYTLTVMAKQLEKTRPDVAERLLHALQPGKETPRLREFLSTHRTILDIQRAFKIKEL

SFKEFLSSVNVIVPRRYSISSGPLEHPNEVSVTVGVVKDIGGADNNTDYYGLASGYLMRC

PIGSKIDAKIKPCKNNFRLPENEQTPVIFICAGTGFAPFRGFLQERHAKGWKSKEKGGSSD

AYLFFGCRHPDHDFIYQKELEEYLEDGTLTKLYTTFSRYNQTKKYVQHLLLTHAQLLFN

LIMNENANIYVCGAGRGMAHDVRRTFERLAVQVAGMSEPEAVDAISHMVDAERYNED

VWG

Nucleotide sequence of ORX85448.1, codon-optimized for
E. coli genome (SEQ ID NO: 4):
ATGAGCAGCCAGAGCGATGAAATTCCGGGCCCGAAACCGCATATTCTGCTGGGTAA

TGTTCAGGATATTATTCCGGATACCATTGGCAATCATCGCCGTCTGCATGATGAATA

TGGCCCGGTTATGCGTCTGTATCTGGGTGGTCATGATTTTGTGAGCATTTGTGATCCG

GAAGTGATTCAGAGCATTACCGGCGAAGGCGATTTTACCAAAGAAATCTATAGCGC

ATACGAAGATCTGGCAATTCTGAGCGGCCGTGGCCTGGTTACCACCGCAACCAAAG

ATCCGGATTGGATTCTGGCCCATAAACTGCTGATGCCGGCCTTTAGTGCCCGCGCAA

TGAAAGCCTATCATGATATTATGGGTAAATGTATTCTGGATCTGCTGAAAATTATGG

AAAGCTATCAGGAATGTGGTGAAGCCATTGATATGAGCCGTTGGATGATTAGCCTG

GCACTGGAAAGTATTGGCGTTATTGGTTTTGGCTATAATTTTAATCTGCTGGATGATA

AAGACAGCGAACGCCATCCGTTTAGCGTTGCACTGAATTATGTGCAGAGTATGATTA

TGAAACGCACCAATAGCGTTACCTGGACCAAATGGCTGCAGACCACCGCCAATGTG

CGTTTTCGTCGCGATCTGGCCACCCTGCGCGATACCGTGGATGATGTGCTGAAACAG

CGTCGTCTGAATCCGCCGAGCGAAGATGCCCGCCGCGATCTGCTGGATTTTATGCTG

GCCGCCGAAAGCAAACAGGGCGAAAAACTGGATGATAATCTGATTCGCGATGAAAT

TATTACCTTTCTGAGTGCAGGCCATAATACCACCAGTAGTTTTCTGAGTTGGACCTTT

TTCGAACTGGCCCGCAATCCGGATGTGGAACAGAAAATTCTGCAGGAAATTGTGAA

TGCCGGCATTAAGCCGGGTGAAATTCCGAGTACCGAACAGGTGGCCAAATGTAAAT

ATATTGATATGGTTATCAAGGAGAGCCTGCGCTTTCATAGCCCGATTCCGCTGGTTA

TTAAGTATTGTCAGAATGATTGCACCATTAAGACCAGTGAAGGTAAAGAATATGAA

ATTAAGCGCGGCCAGCTGGCCCAGATTCAGATTAGCGCCGTGCATAAAGATCCGAA

ACTGTGGGAAAATCCGAATGTGTTTGATCCGGAACGCTTTAATCCGGAAAAAGAAG

CAGATCGTCATCCGTGTGCATGGATTCCGTTTAGCGATGGTCCGCGTGCCTGCATTG

GTCGCCAGTTTAGCCTGCAGGAAGGTAAACTGGCCCTGATTATGCTGCTGTGCAAAT

TTCGTTTTCGTCTGCTGGATGAAACCAAAGAAGTGGGTTATCAGATTATTGTGAGCC

TGAAACCGGTGGATCTGATTATGAAAGTGCTGCCGGCAGAACTGCCGAGTCCGAAT

GCCGGCAGCGATACCAGTAGTGTGAAAGATACCGTTAAACCGCAGCTGAAACCGAA

AGAAAATGAAGTGCTGGAACATGCCCGTTTTCCGCTGCCGCCGGTTACCTTTCTGTA

TGGTACCCAGACCGGCACCAGTGAAGAATATGCACGCAAACTGAGTGGTCAGGCAA

```
AAGAATTTGGCTTTACCGATATTGCCGTGGCAGAACTGGATGATTGGGAAGTTGTTA

AAAATAATCGTATCCCGAGTAATAAGGGTCAGAGTAGTCCGAGCGATGAAGATGGC

ACCAAAGTGAGCCAGCTGGCTGTTATTGTTACCGCAACCTATAATGGTTATCCGCCG

GATAATGCACTGAAATTTGATAGCTGGCTGACCGATATTACCAAAGATCAGAAAAA

TCAGCTGGAAGGTCTGCTGTATGCCGTGTTTGGTTGTGGCAATAAGCAGTGGCAGAG

CACCTTTCAGGCATTTCCGAAAAAAGTGGATGCCAGTATTGAACTGCTGGGCGCAGA

ACGTCTGGTGCCGGCAGGCGCAGGCAATGCCGATCAGGATATTGATGGTGACTTTAC

CAATTGGAGTGCCAGCTTTTGGGCCGCACTGATGCAGAAATATGGCCGCGGCGCCA

GTGATAAAGATGCCGATCTGATGACCACCAGTGGCCCGGTGGCCGATCCGAGTAAT

GATTTTACCCTGGAATTTCTGCCGCTGGGTGGTGACCAGGCAGCAATGGAAGCAGCC

CTGGGTAATCGTAATAGCGATCCGGGCGCACAGGTGGCCATTCTGGAAAATAAGGA

ACTGCAGGATGTTGAAAAAAGTGGCCGTAGTACCCGCCATATTGTTGTTGAATGCCC

GCCGGCCAGCCCGGGCAGTGGTAAAAAAGCAAGTTATCGCGCCGGTGACCATCTGG

AAATTAAGCCGTATAATGATGATCAGCTGGTGGAAAATATTGCCATTGGCTTTGGCT

ATGTTCTGGATAGTGTTTTTCAGATTAAGGATTGCAAAATCACCAATCTGAGTCCGC

GCAGTCTGGCCGCCAATATTATTGGTCCGTGCACCGTTCGCAATGCCCTGACCTATTT

TGCCGATCTGAGTGGTCCGCCGACCCGCTATACCCTGACCGTGATGGCAAAACAGCT

GGAAAAAACCCGCCCGGATGTGGCAGAACGTTTACTGCATGCACTGCAGCCGGGCA

AAGAAACCCCGCGCCTGCGCGAATTTCTGAGTACCCATCGTACCATTCTGGATATTC

AGCGCGCCTTTAAAATTAAGGAACTGAGCTTTAAAGAGTTCCTGAGCAGTGTTAATG

TTATTGTTCCGCGCCGCTATAGTATTAGCAGCGGCCCGCTGGAACATCCGAATGAAG

TGAGTGTGACCGTGGGTGTTGTTAAAGATATTGGCGGTGCAGATAATAATACCGATT

ATTATGGTCTGGCCAGTGGTTATCTGATGCGCTGCCCGATTGGTAGTAAAATTGATG

CCAAAATTAAGCCGTGCAAAATAATTTTCGCCTGCCGGAAAATGAACAGACCCCG

GTTATTTTTATTTGCGCCGGCACCGGCTTTGCCCCGTTTCGTGGTTTTCTGCAGGAAC

GCCATGCCAAAGGTTGGAAAAGTAAAGAAAAAGGCGGTAGTAGCGATGCATATCTG

TTTTTCGGCTGTCGTCATCCGGATCATGATTTTATCTATCAGAAAGAACTGGAAGAA

TACCTGGAAGATGGTACCCTGACCAAACTGTATACCACCTTTAGCCGCTATAATCAG

ACCAAAAAATATGTGCAGCATCTGCTGCTGACCCATGCCCAGCTGCTGTTTAATCTG

ATTATGAATGAAAACGCAAACATCTATGTGTGTGGTGCAGGCCGTGGCATGGCCCAT

GATGTGCGCCGCACCTTTGAACGCCTGGCAGTTCAGGTTGCAGGCATGAGCGAACC

GGAAGCCGTGGATGCCATTAGTCACATGGTTGATGCCGAACGCTATAATGAAGATG

TTTGGGGTTAA
```

*Umbelopsis isabellina* cytochrome P450
Amino acid sequence (SEQ ID NO: 5):

```
MTVYESDKIPGPEPRVLLGNIPDVYPDFVGNITQLHEKYGPVMRLYLGGHDYVSVCDPD

CLQTTHKDGEYFTKEIQSTYEDLAILNGRGLVTTATKDPDWILGHKLLMPAFSARAMKA

YHYKMGDTIKDLLNIIESFQKSGEDFDVSRWMIALALESIGNIGFDYDFNLLKDPNAERH

PFTVALSYVQSMIMKRSASVSWMKWMKTSANARFQRDLGTLRNTLDSVLKERHEHPH

SEDQQSDLLDFMISASTKEGDKLDDKIIRDNVMTFLSAGHNTTSSFLSWTILELCRHPEV

AATIRQELANAGVQPGEIPTPEQVNACKYLDLVIKESLRMHPPIVAVLKYCKKDCTIKAG

TTGDEYKIKAGQLLQSNINALHHSTKVWDEPMVFNPDRFADAELHPNAWMPFSDGPRA
```

-continued

CIGRQFSLQEGKLALVMMLSKFNFSMEDPSQKIGYEIIVAIKPVGLMVKVTPAELPEPTE

EIVVTQRRESKAEPQESLKPAEFPLPPVTILYGTQTNTSEEYAKKLSGQAKEFGFKTIKVD

DLDNWKLLNGGKLTKLNKDQSAPSSGDDVKVSELVVVVTATYNGNPPDNAMKFDEW

LSKKTESIEDTKSNELEGILYAVFGCGNRDWSSTFQKFPTAVDTGLELLGGERLLPAGVG

DASDDIDGDFSEWSANFWSTLMQRYGQSSSGKNADIMTSTAPLADPSKDFNLEFLPVHK

NKELVTQANENRNQRGKTVTIKENRELQNIEKSHRSTKHIEVQFDKSEDGKPLYIAGDH

LEITPVNKEELVELVAVNLGLVLDSVFQIQMNEVDISHLSPRSLAANIKGPCTIRNALKYY

ADLTGPPTRYTLSVLGKQLEKTRPEIAKRLQEALQPGKETPRLKEFLSTHRTFVDIMKAF

NIKELNFKEFLSSVNCIVPRKYSISSGPTEHPFDPSVSIGIVRDIGGPDGKTEYRGLASYL

DTLKPGSQVNAQIKDCKSTFRLPDDGSTPVIFICAGTGMSPFRGFLQERHAQGLKSSKKG

GSSEAYMFFGCRHPDQDFIYKDELQSYVEDGTLTELYTTFSRSNQVVKYVQHSLLQHAQ

MLYELMVDHNAKVYVCGSAGSMAKDVKRTWERITVQMSGMSEPEAEDLLKEWSDKG

KYNEDVWGT

Nucleotide sequence, codon-optimized for *E. coli* genome
(SEQ ID NO: 6):
ATGACCGTGTATGAAAGCGATAAAATTCCGGGTCCGGAACCGCGCGTTCTGCTGGGT

AATATTCCGGATGTTTATCCGGATTTTGTTGGCAATATTACCCAGCTGCATGAAAAA

TATGGTCCGGTTATGCGTCTGTATCTGGGCGGCCATGATTATGTGAGTGTTTGTGATC

CGGATTGTCTGCAGACCACCCATAAAGATGGTGAATATTTTACCAAAGAGATCCAG

AGCACCTATGAAGATCTGGCCATTCTGAATGGCCGTGGCCTGGTGACCACCGCCACC

AAAGATCCGGATTGGATTCTGGGCCATAAACTGCTGATGCCGGCATTTTCAGCCCGC

GCCATGAAAGCCTATCATTATAAAATGGGTGACACCATTAAGGATCTGCTGAATATT

ATTGAAAGTTTTCAGAAGTCCGGTGAAGATTTTGATGTTAGCCGTTGGATGATTGCC

CTGGCACTGGAAAGCATTGGCAATATTGGTTTTGATTATGATTTCAACCTGCTGAAA

GATCCGAATGCCGAACGTCATCCGTTTACCGTTGCCCTGAGTTATGTTCAGAGTATG

ATTATGAAACGCAGTGCAAGCGTTAGCTGGATGAAATGGATGAAAACCAGTGCCAA

TGCCCGCTTTCAGCGTGATCTGGGTACCCTGCGCAATACCCTGGATAGTGTGCTGAA

AGAACGCCATGAACATCCGCATAGCGAAGATCAGCAGAGCGATCTGCTGGATTTTA

TGATTAGTGCCAGTACCAAAGAAGGCGATAAACTGGATGATAAAATTATTCGCGAT

AACGTTATGACCTTTCTGAGCGCAGGTCATAATACCACCAGCAGTTTTCTGAGTTGG

ACCATTCTGGAACTGTGCCGTCATCCGGAAGTTGCCGCAACCATTCGTCAGGAACTG

GCAAATGCCGGTGTGCAGCCGGGTGAAATTCCGACCCCGGAACAGGTGAATGCCTG

TAAATATCTGGATCTGGTTATTAAGGAAAGCCTGCGTATGCATCCGCCGATTGTGGC

AGTTCTGAAATATTGTAAAAAGGATTGTACCATCAAGGCCGGTACCACCGGTGACG

AATATAAAATTAAGGCAGGCCAGCTGCTGCAGAGCAATATTAATGCACTGCATCAT

AGCACCAAAGTTTGGGATGAACCGATGGTTTTTAATCCGGATCGTTTTGCCGATGCA

GAACTGCATCCGAATGCCTGGATGCCGTTTAGTGATGGTCCGCGTGCCTGTATTGGC

CGTCAGTTTAGCCTGCAGGAAGGCAAACTGGCACTGGTTATGATGCTGAGCAAATTC

AATTTTAGCATGGAAGATCCGAGCCAGAAAATTGGCTATGAAATTATTGTGGCCATT

AAGCCGGTGGGCCTGATGGTGAAAGTGACCCCGGCCGAACTGCCGGAACCGACCGA

AGAAATTGTTGTTACCCAGCGCCGTGAAAGTAAAGCAGAACCGCAGGAAAGTCTGA

AACCGGCCGAATTTCCGCTGCCGCCGGTTACCATTCTGTATGGCACCCAGACCAATA

```
CCAGCGAAGAATATGCAAAAAAGCTGAGCGGCCAGGCCAAAGAATTTGGTTTTAAA

ACCATTAAGGTGGATGATCTGGATAATTGGAAACTGCTGAATGGCGGTAAACTGAC

CAAACTGAATAAGGATCAGAGTGCACCGAGTAGTGGTGACGATGTGAAAGTGAGTG

AACTGGTGGTGGTTGTTACCGCAACCTATAATGGCAATCCGCCGGATAATGCAATGA

AATTTGATGAATGGCTGAGTAAAAAGACCGAAAGCATTGAAGATACCAAAAGCAAT

GAACTGGAAGGCATTCTGTATGCAGTTTTTGGCTGCGGCAATCGTGATTGGAGCAGT

ACCTTTCAGAAATTTCCGACCGCAGTGGATACCGGTCTGGAACTGCTGGGCGGCGAA

CGTCTGCTGCCGGCAGGCGTTGGCGATGCCAGTGATGATATTGATGGCGATTTTAGC

GAATGGAGCGCAAATTTTTGGAGTACCCTGATGCAGCGTTATGGTCAGAGCAGTAG

CGGCAAAAATGCAGATATTATGACCAGCACCGCACCGCTGGCAGATCCGAGTAAAG

ATTTTAATCTGGAATTTCTGCCGGTGCATAAAAATAAGGAACTGGTGACCCAGGCAA

ATGAAAATCGCAATCAGCGCGGTAAAACCGTGACCATTAAGGAAAATCGCGAACTG

CAGAATATTGAAAAAGCCATCGTAGTACCAAACATATTGAAGTTCAGTTTGATAA

GAGCGAAGATGGTAAACCGCTGTATATTGCCGGTGACCATCTGGAAATTACCCCGGT

TAATAAGGAAGAACTGGTTGAACTGGTGGCCGTTAATCTGGGTCTGGTGCTGGATAG

CGTGTTTCAGATTCAGATGAATGAAGTTGATATTAGTCACCTGAGCCCGCGCAGTCT

GGCAGCAAATATTAAGGGCCCGTGCACCATTCGCAATGCACTGAAATATTATGCAG

ATCTGACCGGTCCGCCGACCCGTTATACCCTGAGTGTGCTGGGTAAACAGCTGGAAA

AAACCCGTCCGGAAATTGCCAAACGTCTGCAGGAAGCCCTGCAGCCGGGCAAAGAA

ACCCCGCGCCTGAAAGAATTTCTGAGTACCCATCGTACCTTTGTTGATATTATGAAA

GCATTCAATATCAAGGAGCTGAATTTTAAAGAGTTCCTGAGCAGTGTGAATTGTATT

GTGCCGCGCAAATATAGCATTAGTAGTGGTCCGACCGAACATCCGTTTGATCCGAGC

GTGAGCATTGGTATTGTTCGCGATATTGGTGGTCCGGATGGCAAAACCGAATATCGC

GGTCTGGCAAGCGGCTATCTGGATACCCTGAAACCGGGTAGTCAGGTGAATGCGCA

GATTAAGGATTGTAAAAGTACCTTTCGCCTGCCGGATGATGGTAGCACCCCGGTTAT

TTTTATTTGCGCCGGTACCGGCATGAGCCCGTTTCGTGGCTTTCTGCAGGAACGCCAT

GCCCAGGGTCTGAAAAGCAGTAAAAAAGGTGGCAGTAGTGAAGCATATATGTTTTT

CGGTTGCCGCCATCCGGATCAGGATTTTATCTATAAAGATGAACTGCAGAGTTACGT

TGAAGATGGTACCCTGACCGAACTGTATACCACCTTTAGTCGTAGTAATCAGGTGGT

TAAATATGTGCAGCATAGCCTGCTGCAGCATGCACAGATGCTGTATGAACTGATGGT

GGATCATAATGCAAAAGTTTATGTTTGTGGCAGCGCCGGTAGCATGGCAAAAGATG

TTAAACGCACCTGGGAACGCATTACCGTTCAGATGAGTGGCATGAGCGAACCGGAA

GCCGAAGATCTGCTGAAAGAATGGAGCGATAAAGGCAAATATAATGAAGATGTGTG

GGGCACCTAA
```

The invention claimed is:

1. A method for producing a C4-C20 gamma lactone, the method comprising:
   providing a reaction mixture comprising a recombinant CYP450 protein having carboxylic acid 4-hydroxylase activity and a C4-C20 carboxylic acid substrate to provide a 4-hydroxy C4-C20 carboxylic acid; and
   subjecting the 4-hydroxy C4-C20 carboxylic acid to acidic conditions to produce the C4-C20 gamma lactone,
   wherein the recombinant CYP450 protein comprises an amino acid sequence having at least 90% identity to SEQ ID NO: 1.

2. The method of claim 1, wherein the recombinant CYP450 protein is expressed by a transformed isolated host cell in the reaction mixture.

3. The method of claim 2, wherein the recombinant CYP450 protein comprises an amino acid sequence having at least 95% identity to SEQ ID NO: 1.

4. The method of claim 1, wherein the recombinant CYP450 protein comprises an amino acid sequence having at least 98% identity to SEQ ID NO: 1.

5. The method of claim 1, wherein the C4-C20 carboxylic acid substrate comprises a C4-C20 carboxylic acid; a salt of a C4-C20 carboxylic acid; an ester of a C4-C20 carboxylic acid; a mono-, di- or triglyceride of a C4-C20 carboxylic acid; or a combination thereof.

6. The method of claim 1, wherein the C4-C20 carboxylic acid comprises a straight-chain C4-C20 carboxylic acid, a branched C4-C20 carboxylic acid, a saturated C4-C20 carboxylic acid, an unsaturated C4-C20 carboxylic acid, or a combination thereof.

7. The method of claim 4 for producing a C4-C20 gamma lactone selected from γ-heptalactone, γ-octalactone, γ-nonalactone, γ-decalactone, γ-undecalactone, γ-dodecalactone, γ-tridecalactone, and γ-tetradecalactone, wherein the C4-C20 carboxylic acid substrate is selected from heptanoic acid, octanoic acid, nonanoic acid, decanoic acid, undecanoic acid, dodecanoic acid, tridecanoic acid, and tetradecanoic acid.

8. The method of claim 1 for producing a C4-C20 gamma lactone selected from γ-undecalactone and γ-undecenolactone, wherein the C4-C20 carboxylic acid substrate is selected from undecanoic acid and undecenoic acid.

9. The method of claim 1 for producing a C4-C20 gamma lactone selected from γ-hexalactone, γ-heptalactone, γ-decalactone, γ-undecalactone, γ-dodecalactone, γ-tridecalactone, and γ-tetradecalactone, wherein the C4-C20 carboxylic acid substrate is selected from hexanoic acid, heptanoic acid, decanoic acid, undecanoic acid, dodecanoic acid, tridecanoic acid, and tetradecanoic acid.

10. The method of claim 2, wherein the transformed isolated host cell is selected from a bacterial cell and a yeast cell.

11. The method of claim 2, wherein the transformed isolated host cell is selected from a group comprising of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Mucor; Pantoea; Corynebacterium*; and *Clostridium*.

12. The method of claim 1, wherein the recombinant CYP450 protein comprises the amino acid sequence of SEQ ID NO: 1.

* * * * *

SEQUENCE LISTING

<160> NUMBER OF SEQ ID NOS: 6

<210> SEQ ID NO 1
<211> LENGTH: 1137
<212> TYPE: PRT
<213> ORGANISM: Mucor amibiguus

```
<400> SEQUENCE: 1

Met Thr Lys Tyr Ala His Asp Gln Ile Pro Gly Pro Glu Pro His Tyr
1               5                   10                  15

Leu Leu Gly Asn Val Pro Asp Ile Phe Pro Asp Ser Leu Gly Asn Leu
            20                  25                  30

Ile Lys Leu His Asp Lys Tyr Gly Pro Ile Val His Leu Ser Met Gly
        35                  40                  45

Gly His Glu Leu Leu Ser Val Asp Asp Pro Ala Val Leu Glu Thr Ile
    50                  55                  60

Cys Glu Asp Asn Glu Tyr Phe Thr Lys Glu Ile Glu Ser Val Tyr Ser
65                  70                  75                  80

Asp Leu Ala Ile Leu Asn Gly Arg Gly Leu Val Thr Thr Ser Thr Ala
                85                  90                  95

Asp Pro Asp Trp Gln Leu Gly His Lys Leu Ile Met Asn Ala Phe Ser
            100                 105                 110

Ala Arg Ala Met Lys Ala Tyr His Tyr Lys Met Gly Glu Ser Ile Ser
        115                 120                 125

Glu Leu Cys Glu Ile Met Asp Ser Phe Ala Lys Ser Gly Glu Asp Phe
    130                 135                 140

Asp Val Ser Arg Trp Phe Ile Ala Leu Ala Leu Glu Ser Ile Gly Lys
145                 150                 155                 160

Ile Gly Phe Asp Tyr Asp Phe Asp Leu Leu Lys Asp Pro Asn Ala Pro
                165                 170                 175

Arg His Pro Phe Thr Val Ala Leu Ala Tyr Val Gln Ser Met Ile Met
            180                 185                 190

Lys Arg Ala Ser Thr Leu Ser Trp Leu Lys Trp Tyr Gln Thr Thr Thr
        195                 200                 205

Asn Val Arg Phe His Arg Asp Leu Gln Thr Leu Arg Gly Thr Val Glu
    210                 215                 220

Glu Val Leu Lys Asp Arg Arg Glu His Pro His Thr Glu Ala Asp Gln
225                 230                 235                 240

Ser Asp Leu Leu Asp Phe Met Ile Lys Ala Glu Ser Lys Glu Gly Glu
                245                 250                 255

Lys Leu Asn Asp Ser Leu Ile Arg Asp Asn Ile Ile Thr Phe Leu Ser
            260                 265                 270

Ala Gly His Asn Thr Thr Ser Ala Phe Leu Ser Trp Thr Met Leu Glu
        275                 280                 285

Leu Cys Lys His Pro Glu Val Val Glu Asn Ile Lys Gln Glu Ile Ala
    290                 295                 300

Asn Cys Gly Ile Lys Ala Gly Glu Val Pro Thr Pro Glu Gln Val Lys
305                 310                 315                 320

Glu Cys Lys Tyr Leu Asp Leu Val Ile Lys Glu Ser Leu Arg Ile His
                325                 330                 335

Pro Pro Ile Thr Ser Ile Leu Lys Tyr Cys Lys Lys Asp Ala Thr Val
            340                 345                 350

Lys Ala Ser Asn Gly Asp Glu Tyr Asp Ile Lys Ala Gly Gln Leu Leu
        355                 360                 365

Gln Val Asn Ile Asn Ala Leu His His Asn Pro Lys Val Trp Glu Asp
    370                 375                 380

Pro Asp Val Phe Asn Pro Asp Arg Phe Ser Gly Asp Thr Asp Asn Leu
385                 390                 395                 400

Pro Asn Thr Ala Trp Leu Thr Phe Ser Thr Gly Pro Arg Ala Cys Ile
                405                 410                 415
```

```
Gly Arg Gln Phe Ala Leu Gln Glu Gly Lys Leu Ala Leu Val Met Ile
                420                 425                 430

Leu Ser Arg Phe His Phe Lys Met Asp Asp Pro Ser Gln Lys Ile Gly
            435                 440                 445

Tyr Ala Val Val Val Ser Thr Lys Pro Val Gly Phe Phe Ala Lys Ile
        450                 455                 460

Glu Ser Ser Gln Leu Pro Glu Pro Thr Glu Glu Ile Val Val Thr Lys
465                 470                 475                 480

Arg Arg Glu Ser Lys Ala Val Pro Gln Glu Lys Val Lys Pro Ala Glu
                485                 490                 495

Phe Pro Leu Pro Pro Val Thr Phe Leu Phe Gly Thr Gln Thr Asn Thr
            500                 505                 510

Ser Glu Glu Tyr Ala Arg Lys Leu Ser Gly Gln Ala Lys Glu Met Gly
        515                 520                 525

Phe Lys Glu Val Thr Val Gln Asp Leu Asp Asp Trp Lys Leu Val Lys
    530                 535                 540

Gly Glu Ala Ile Ala Lys Ala Gln His Asp Ala Asp Ala Pro Ser Ser
545                 550                 555                 560

Glu Asp Asp Val Lys Val Ser Glu Leu Val Val Val Thr Ala Thr
                565                 570                 575

Tyr Asn Gly Phe Pro Pro Asp Asp Ala Asn Glu Phe Ala Lys Trp Leu
        580                 585                 590

Asp Glu Arg Thr Lys Asp Ser Glu Ala Thr Lys Asn Asn Met Leu Ser
            595                 600                 605

Gly Met Leu Tyr Ala Val Phe Gly Cys Gly Asn Arg Asp Trp Thr Ser
        610                 615                 620

Thr Phe Gln Lys Phe Pro Lys Lys Val Asp Ser Gly Phe Glu Leu Leu
625                 630                 635                 640

Gly Gly Glu Arg Leu Leu Pro Ala Gly Glu Gly Asp Ala Ser Asp Asp
                645                 650                 655

Ile Asp Gly Asp Phe Ser Leu Trp Ser Ala Ser Phe Trp Thr Ala Leu
            660                 665                 670

Met Gln Arg Tyr Gly Gln Ser Ser Ser Gly Lys Asn Ala Asp Ile Met
        675                 680                 685

Ser Asn Asn Gly Pro Ala Ala Asp Pro Ser Gln Asp Phe Thr Leu Glu
690                 695                 700

Phe Ile Asn Ile Val Lys Glu Lys Val Lys Thr Glu Gln Ala Ala Leu
705                 710                 715                 720

Asn Cys Asn Gln Leu Glu Thr Val Ala Thr Ile Val Glu Asn Arg Glu
                725                 730                 735

Leu Gln His Thr Glu Lys Ser His Arg Ser Thr Arg His Ile Gln Val
            740                 745                 750

Gln Phe Asp Lys Ser Val Asp Gly Lys Pro Leu Tyr Glu Ala Gly Asp
        755                 760                 765

His Leu Glu Val Val Pro Val Asn Glu Asp Arg Leu Val Glu Ile Ile
    770                 775                 780

Ala Thr Asn Leu Gly Leu Val Leu Asp Ser Val Phe Glu Val Lys Asp
785                 790                 795                 800

Leu Asp Ile Lys Asn Leu Ser Pro Arg Ser Val Ala Ala Asn Ile Lys
                805                 810                 815

Gly Pro Cys Thr Ile Arg Asn Ala Leu Lys Tyr Tyr Ala Asp Leu Thr
            820                 825                 830
```

-continued

Gly Pro Pro Thr Arg Phe Ser Leu Ser Ile Leu Ser Lys Gln Leu Lys
        835                 840                 845

Asp Ser Arg Pro Asp Ile Ala Glu Arg Leu Gln Lys Ala Leu Gln Pro
850                 855                 860

Gly Lys Glu Thr Glu Arg Leu Lys Glu Phe Leu Ala Ser His Arg Thr
865                 870                 875                 880

Leu Ile Asp Ile Ile Gln Ala Phe Lys Ile Lys Glu Leu Asn Phe Lys
                885                 890                 895

Glu Phe Ile Ser Ser Val Asn Cys Ile Val Pro Arg Lys Tyr Ser Ile
            900                 905                 910

Ser Ser Gly Pro Leu Glu His Pro Phe Asp Pro Ser Ile Ser Val Gly
        915                 920                 925

Val Val Asp Thr Val Gly Gly Pro Asp Gly Asn Thr His Tyr Phe Gly
    930                 935                 940

Leu Ala Ser Gly Tyr Leu Ser His Gln Glu Pro Gly Thr Lys Ile Asn
945                 950                 955                 960

Ala Gln Ile Lys Ala Cys Lys Ser Thr Phe Arg Leu Pro Asp Asp Pro
                965                 970                 975

Ser Thr Pro Val Ile Phe Ile Ala Ala Gly Thr Gly Phe Ser Pro Phe
            980                 985                 990

Arg Gly Phe Leu Gln Glu Arg His Ala Lys Gly Leu Lys Ser Ser Lys
        995                 1000                1005

Lys Asn Ser Asn Gly Glu Ser Ser Glu Cys Tyr Met Phe Phe Gly
    1010                1015                1020

Cys Arg His Pro Asp Gln Asp Phe Ile Tyr Lys Glu Glu Phe Asp
    1025                1030                1035

Ala Tyr Leu Glu Asp Gly Thr Ile Thr Glu Leu Tyr Thr Thr Phe
    1040                1045                1050

Ser Arg Ser Gly Glu Val Val Lys Tyr Val Gln His Ala Leu Leu
    1055                1060                1065

Lys His Ala Asn Leu Leu Tyr Lys Leu Met Glu Glu Ser Asn Ala
    1070                1075                1080

Lys Val Tyr Ile Cys Gly Ser Ala Gly Ser Met Ala Lys Asp Val
    1085                1090                1095

Lys Arg Thr Trp Glu Arg Leu Leu Val Gln Met Ser Gly Val Ser
    1100                1105                1110

Glu Ser Glu Ala Ala Glu Gln Ile Gln Ala Trp Val Asp Glu Gly
    1115                1120                1125

Lys Tyr Asn Glu Asp Val Trp Gly Thr
    1130                1135

<210> SEQ ID NO 2
<211> LENGTH: 3414
<212> TYPE: DNA
<213> ORGANISM: Mucor amibiguus

<400> SEQUENCE: 2
atgaccaaat atgcccatga tcagattccg ggtcctgaac cgcattatct gctgggtaat      60
gttccggata tttttccgga tagcctgggc aatctgatta aactgcatga taaatatggt     120
ccgattgtgc atctgagcat gggtggtcat gaactgctga gcgttgatga tccggcagtt     180
ctggaaacca tttgtgaaga taatgaatat tcaccaaaag aaatcgaaag cgtgtatagc     240
gatctggcaa ttctgaatgg tcgtggtctg gttaccacca gtaccgcaga tccggattgg     300
cagctgggtc ataaactgat tatgaatgca tttagcgcac gtgccatgaa agcctatcac     360

-continued

```
tataaaatgg gtgaaagcat tagcgaactg tgcgaaatta tggatagctt tgcaaaaagc    420
ggtgaggatt ttgatgttag ccgttggttt attgcactgg cactggaaag cattggtaaa    480
atcggtttcg attatgattt cgacctgctg aaagatccga atgcaccgcg tcatccgttt    540
accgttgcgc tggcctatgt tcagagtatg atcatgaaac gtgcaagcac cctgagctgg    600
ctgaaatggt atcagaccac caccaatgtt cgttttcatc gtgatctgca gaccctgcgt    660
ggcaccgttg aagaagttct gaaagaccgt cgtgaacatc cgcataccga agcagatcag    720
agcgatctgc tggattttat gattaaagcc gaaagcaaag aaggcgagaa actgaacgat    780
agcctgattc gtgataacat cattaccttt ctgagcgcag gtcataatac cacctcagca    840
tttctgagct ggaccatgct ggaactgtgt aaacatccgg aagttgtcga aaacatcaaa    900
caagaaattg ccaactgcgg tattaaagcg ggtgaagttc cgacaccgga acaggttaaa    960
gaatgtaaat atctggacct ggtgatcaaa gaaagcctgc gtattcatcc gcctattacc   1020
agcattctga atactgtaa aaaagacgca accgtgaaag ccagcaatgg tgatgaatat    1080
gatattaaag caggtcagct gctgcaggtt aacattaatg cactgcatca taacccgaaa   1140
gtttgggaag atcctgatgt ttttaacccg gatcgtttta gcggtgatac cgataatctg   1200
ccgaataccg catggctgac ctttagcacc ggtccgcgtg catgtattgg tcgtcagttt   1260
gcactgcaag aaggtaaact ggccctggtt atgattctga gccgttttca tttcaaaatg   1320
gatgatccga gccagaaaat tggttatgca gttgttgtta gcaccaaacc ggttggtttt   1380
tttgccaaaa ttgaaagcag ccagctgccg gaaccgaccg aagaaattgt tgttaccaaa   1440
cgtcgtgaaa gtaaagcagt tccgcaagaa aaagttaaac cggcagaatt tccgctgcct   1500
ccggtgacct ttctgtttgg cacccagacc aataccagcg aagaatatgc acgtaaactg   1560
agcggtcagg caaagaaat gggttttaaa gaagttaccg tccaggatct ggatgattgg   1620
aaactggtta aggtgaagc aattgcaaaa gcacagcatg atgccgatgc accgagcagc   1680
gaagatgatg ttaaagtgag cgaactggtt gttgttgtga ccgcaaccta taatggtttt   1740
ccgcctgatg atgcaaacga atttgcaaaa tggctggatg aacgtaccaa agatagcgaa   1800
gcaaccaaaa ataacatgct gagcggtatg ctgtatgcag tgtttggttg tggtaatcgt   1860
gattggacca gcacctttca gaaattcccg aaaaaagttg atagcggctt tgaactgtta   1920
ggtggtgaac gtctgctgcc agccggtgaa ggtgatgcaa gtgatgatat tgatggtgat   1980
tttagcctgt ggtctgccag cttttggacc gcactgatgc agcgttatgg tcagagcagc   2040
agcggtaaaa atgcagatat tatgagcaat aatggtccgg cagcagatcc gagtcaggat   2100
tttaccctgg aatttatcaa catcgtgaaa gagaaggtca aaaccgaaca ggcagcactg   2160
aattgtaatc agctggaaac cgttgcaacc attgttgaaa atcgcgaact gcagcataca   2220
gaaaaaagcc atcgtagcac ccgtcatatt caggttcagt ttgataaaag cgtggatggt   2280
aaaccgctgt atgaagccgg tgatcatctg gaagtggttc cggttaatga agatcgtctg   2340
gttgaaatta ttgccaccaa tctgggttta gttctggata gcgttttga ggtgaaagac    2400 ctggatatta agaatctgag tccgcgtagc gttgcagcaa acattaaagg tccgtgtacc   2460
attcgtaatg ccctgaaata ttacgcagat ctgaccggtc ctccgacacg ttttagtctg   2520
agcattctgt caaaacagct gaaagacagc cgtcctgata ttgcagaacg cctgcagaaa   2580
gcactgcagc ctggtaaaga aaccgaacgt ctgaaagaat ttctggcaag tcatcgtacc   2640
ctgatcgata ttattcaggc cttcaaaatc aaagaactga acttcaaaga gtttatcagc   2700
agcgttaatt gcatcgttcc gcgtaaatat agcattagca gtggtccgct ggaacatccg   2760
```

```
tttgatccga gtattagcgt tggtgttgtt gataccgttg gtggtccgga tggtaatacc    2820
cattattttg gtctggcaag cggttatctg agccatcaag aacccgggtac aaaaatcaat    2880 gcacagatta aagcatgcaa gagtaccttt cgtctgccgg atgatcctag cacaccggtt    2940
atctttattg cagcaggcac cggttttagc ccgtttcgtg gttttctgca agaacgtcat    3000
gcaaaaggtc tgaaaagcag caaaaaaaac agcaatggcg aaagcagcga gtgctatatg    3060
ttttttggct gtcgtcatcc ggatcaggat ttcatctata agaagaatt  tgacgcctac    3120 ctggaagatg gcaccattac agaactgtat accacccttta gccgtagcgg tgaagttgtt    3180
aaatatgttc agcacgcact gctgaaacat gcaaatctgc tgtacaaact gatggaagaa    3240
agcaacgcca aagtgtatat ttgtggtagc gcaggtagca tggcaaaaga tgttaaacgt    3300
acctgggagc gcctgctggt tcagatgagc ggtgttagcg aaagcgaagc agcagagcag    3360
attcaggcat gggttgatga aggcaaatat aacgaagatg tttgggggcac ctaa          3414
```

<210> SEQ ID NO 3
<211> LENGTH: 1136
<212> TYPE: PRT
<213> ORGANISM: Basidiobolus meristosporus

<400> SEQUENCE: 3

```
Met Ser Ser Gln Ser Asp Glu Ile Pro Gly Pro Lys Pro His Ile Leu
1               5                   10                  15

Leu Gly Asn Val Gln Asp Ile Ile Pro Asp Thr Ile Gly Asn His Arg
            20                  25                  30

Arg Leu His Asp Glu Tyr Gly Pro Val Met Arg Leu Tyr Leu Gly Gly
        35                  40                  45

His Asp Phe Val Ser Ile Cys Asp Pro Glu Val Ile Gln Ser Ile Thr
    50                  55                  60

Gly Glu Gly Asp Phe Thr Lys Glu Ile Tyr Ser Ala Tyr Glu Asp Leu
65                  70                  75                  80

Ala Ile Leu Ser Gly Arg Gly Leu Val Thr Thr Ala Thr Lys Asp Pro
                85                  90                  95

Asp Trp Ile Leu Ala His Lys Leu Leu Met Pro Ala Phe Ser Ala Arg
            100                 105                 110

Ala Met Lys Ala Tyr His Asp Ile Met Gly Lys Cys Ile Leu Asp Leu
        115                 120                 125

Leu Lys Ile Met Glu Ser Tyr Gln Glu Cys Gly Glu Ala Ile Asp Met
    130                 135                 140

Ser Arg Trp Met Ile Ser Leu Ala Leu Glu Ser Ile Gly Val Ile Gly
145                 150                 155                 160

Phe Gly Tyr Asn Phe Asn Leu Leu Asp Asp Lys Asp Ser Glu Arg His
                165                 170                 175

Pro Phe Ser Val Ala Leu Asn Tyr Val Gln Ser Met Ile Met Lys Arg
            180                 185                 190

Thr Asn Ser Val Thr Trp Thr Lys Trp Leu Gln Thr Ala Asn Val
        195                 200                 205

Arg Phe Arg Arg Asp Leu Ala Thr Leu Arg Asp Thr Val Asp Asp Val
    210                 215                 220

Leu Lys Gln Arg Arg Leu Asn Pro Pro Ser Glu Asp Ala Arg Arg Asp
225                 230                 235                 240

Leu Leu Asp Phe Met Leu Ala Ala Glu Ser Lys Gln Gly Glu Lys Leu
                245                 250                 255
```

```
Asp Asp Asn Leu Ile Arg Asp Glu Ile Ile Thr Phe Leu Ser Ala Gly
            260                 265                 270

His Asn Thr Thr Ser Ser Phe Leu Ser Trp Thr Phe Glu Leu Ala
        275                 280                 285

Arg Asn Pro Asp Val Glu Gln Lys Ile Leu Gln Glu Ile Val Asn Ala
        290                 295                 300

Gly Ile Lys Pro Gly Glu Ile Pro Ser Thr Glu Gln Val Ala Lys Cys
305                 310                 315                 320

Lys Tyr Ile Asp Met Val Ile Lys Glu Ser Leu Arg Phe His Ser Pro
                325                 330                 335

Ile Pro Leu Val Ile Lys Tyr Cys Gln Asn Asp Cys Thr Ile Lys Thr
            340                 345                 350

Ser Glu Gly Lys Glu Tyr Glu Ile Lys Arg Gly Gln Leu Ala Gln Ile
        355                 360                 365

Gln Ile Ser Ala Val His Lys Asp Pro Lys Leu Trp Glu Asn Pro Asn
    370                 375                 380

Val Phe Asp Pro Glu Arg Phe Asn Pro Glu Lys Glu Ala Asp Arg His
385                 390                 395                 400

Pro Cys Ala Trp Ile Pro Phe Ser Asp Gly Pro Arg Ala Cys Ile Gly
                405                 410                 415

Arg Gln Phe Ser Leu Gln Glu Gly Lys Leu Ala Leu Ile Met Leu Leu
            420                 425                 430

Cys Lys Phe Arg Phe Arg Leu Leu Asp Glu Thr Lys Glu Val Gly Tyr
        435                 440                 445

Gln Ile Ile Val Ser Leu Lys Pro Val Asp Leu Ile Met Lys Val Leu
    450                 455                 460

Pro Ala Glu Leu Pro Ser Pro Asn Ala Gly Ser Asp Thr Ser Ser Val
465                 470                 475                 480

Lys Asp Thr Val Lys Pro Gln Leu Lys Pro Lys Glu Asn Glu Val Leu
                485                 490                 495

Glu His Ala Arg Phe Pro Leu Pro Pro Val Thr Phe Leu Tyr Gly Thr
            500                 505                 510

Gln Thr Gly Thr Ser Glu Glu Tyr Ala Arg Lys Leu Ser Gly Gln Ala
        515                 520                 525

Lys Glu Phe Gly Phe Thr Asp Ile Ala Val Ala Glu Leu Asp Asp Trp
    530                 535                 540

Glu Val Val Lys Asn Asn Arg Ile Pro Ser Asn Lys Gly Gln Ser Ser
545                 550                 555                 560

Pro Ser Asp Glu Asp Gly Thr Lys Val Ser Gln Leu Ala Val Ile Val
                565                 570                 575

Thr Ala Thr Tyr Asn Gly Tyr Pro Pro Asp Asn Ala Leu Lys Phe Asp
            580                 585                 590

Ser Trp Leu Thr Asp Ile Thr Lys Asp Gln Lys Asn Gln Leu Glu Gly
        595                 600                 605

Leu Leu Tyr Ala Val Phe Gly Cys Gly Asn Lys Gln Trp Gln Ser Thr
    610                 615                 620

Phe Gln Ala Phe Pro Lys Lys Val Asp Ala Ser Ile Glu Leu Leu Gly
625                 630                 635                 640

Ala Glu Arg Leu Val Pro Ala Gly Ala Gly Asn Ala Asp Gln Asp Ile
                645                 650                 655

Asp Gly Asp Phe Thr Asn Trp Ser Ala Ser Phe Trp Ala Ala Leu Met
            660                 665                 670
```

-continued

```
Gln Lys Tyr Gly Arg Gly Ala Ser Asp Lys Asp Ala Asp Leu Met Thr
            675                 680                 685
Thr Ser Gly Pro Val Ala Asp Pro Ser Asn Asp Phe Thr Leu Glu Phe
690                 695                 700
Leu Pro Leu Gly Gly Asp Gln Ala Ala Met Glu Ala Ala Leu Gly Asn
705                 710                 715                 720
Arg Asn Ser Asp Pro Gly Ala Gln Val Ala Ile Leu Glu Asn Lys Glu
                725                 730                 735
Leu Gln Asp Val Glu Lys Ser Gly Arg Ser Thr Arg His Ile Val Val
            740                 745                 750
Glu Cys Pro Pro Ala Ser Pro Gly Ser Gly Lys Lys Ala Ser Tyr Arg
            755                 760                 765
Ala Gly Asp His Leu Glu Ile Lys Pro Tyr Asn Asp Asp Gln Leu Val
            770                 775                 780
Glu Asn Ile Ala Ile Gly Phe Gly Tyr Val Leu Asp Ser Val Phe Gln
785                 790                 795                 800
Ile Lys Asp Cys Lys Ile Thr Asn Leu Ser Pro Arg Ser Leu Ala Ala
                805                 810                 815
Asn Ile Ile Gly Pro Cys Thr Val Arg Asn Ala Leu Thr Tyr Phe Ala
            820                 825                 830
Asp Leu Ser Gly Pro Pro Thr Arg Tyr Thr Leu Thr Val Met Ala Lys
835                 840                 845
Gln Leu Glu Lys Thr Arg Pro Asp Val Ala Glu Arg Leu Leu His Ala
            850                 855                 860
Leu Gln Pro Gly Lys Glu Thr Pro Arg Leu Arg Glu Phe Leu Ser Thr
865                 870                 875                 880
His Arg Thr Ile Leu Asp Ile Gln Arg Ala Phe Lys Ile Lys Glu Leu
                885                 890                 895
Ser Phe Lys Glu Phe Leu Ser Ser Val Asn Val Ile Val Pro Arg Arg
            900                 905                 910
Tyr Ser Ile Ser Ser Gly Pro Leu Glu His Pro Asn Glu Val Ser Val
            915                 920                 925
Thr Val Gly Val Val Lys Asp Ile Gly Gly Ala Asp Asn Thr Asp
930                 935                 940
Tyr Tyr Gly Leu Ala Ser Gly Tyr Leu Met Arg Cys Pro Ile Gly Ser
945                 950                 955                 960
Lys Ile Asp Ala Lys Ile Lys Pro Cys Lys Asn Asn Phe Arg Leu Pro
                965                 970                 975
Glu Asn Glu Gln Thr Pro Val Ile Phe Ile Cys Ala Gly Thr Gly Phe
            980                 985                 990
Ala Pro Phe Arg Gly Phe Leu Gln Glu Arg His Ala Lys Gly Trp Lys
            995                 1000                1005
Ser Lys Glu Lys Gly Gly Ser Ser Asp Ala Tyr Leu Phe Phe Gly
    1010                1015                1020
Cys Arg His Pro Asp His Asp Phe Ile Tyr Gln Lys Glu Leu Glu
    1025                1030                1035
Glu Tyr Leu Glu Asp Gly Thr Leu Thr Lys Leu Tyr Thr Thr Phe
    1040                1045                1050
Ser Arg Tyr Asn Gln Thr Lys Lys Tyr Val Gln His Leu Leu Leu
    1055                1060                1065
Thr His Ala Gln Leu Leu Phe Asn Leu Ile Met Asn Glu Asn Ala
    1070                1075                1080
```

-continued

| Asn | Ile | Tyr | Val | Cys | Gly | Ala | Gly | Arg | Gly | Met | Ala | His | Asp | Val |
|-----|-----|-----|-----|-----|-----|-----|-----|-----|-----|-----|-----|-----|-----|-----|
| 1085 | | | | | 1090 | | | | | 1095 | | | | |

| Arg | Arg | Thr | Phe | Glu | Arg | Leu | Ala | Val | Gln | Val | Ala | Gly | Met | Ser |
|-----|-----|-----|-----|-----|-----|-----|-----|-----|-----|-----|-----|-----|-----|-----|
| 1100 | | | | | 1105 | | | | | 1110 | | | | |

| Glu | Pro | Glu | Ala | Val | Asp | Ala | Ile | Ser | His | Met | Val | Asp | Ala | Glu |
|-----|-----|-----|-----|-----|-----|-----|-----|-----|-----|-----|-----|-----|-----|-----|
| 1115 | | | | | 1120 | | | | | 1125 | | | | |

| Arg | Tyr | Asn | Glu | Asp | Val | Trp | Gly |
|-----|-----|-----|-----|-----|-----|-----|-----|
| 1130 | | | | | 1135 | | |

<210> SEQ ID NO 4
<211> LENGTH: 3411
<212> TYPE: DNA
<213> ORGANISM: Basidiobolus meristosporus

<400> SEQUENCE: 4

| | |
|---|---|
| atgagcagcc agagcgatga aattccgggc ccgaaaccgc atattctgct gggtaatgtt | 60 |
| caggatatta ttccggatac cattggcaat catcgccgtc tgcatgatga atatggcccg | 120 |
| gttatgcgtc tgtatctggg tggtcatgat tttgtgagca tttgtgatcc ggaagtgatt | 180 |
| cagagcatta ccggcgaagg cgattttacc aaagaaatct atagcgcata cgaagatctg | 240 |
| gcaattctga gcggccgtgg cctggttacc accgcaacca agatccgga ttggattctg | 300 |
| gcccataaac tgctgatgcc ggcctttagt gcccgcgcaa tgaaagccta tcatgatatt | 360 |
| atgggtaaat gtattctgga tctgctgaaa attatgaaa gctatcagga atgtggtgaa | 420 |
| gccattgata tgagccgttg atgattagc ctggcactgg aaagtattgg cgttattggt | 480 |
| tttggctata attttaatct gctggatgat aaagacagcg aacgccatcc gtttagcgtt | 540 |
| gcactgaatt atgtgcagag tatgattatg aaacgcacca atagcgttac ctggaccaaa | 600 |
| tggctgcaga ccaccgccaa tgtgcgtttt cgtcgcgatc tggccaccct gcgcgatacc | 660 |
| gtggatgatg tgctgaaaca gcgtcgtctg aatccgccga gcgaagatgc ccgccgcgat | 720 |
| ctgctggatt ttatgctggc cgccgaaagc aaacagggcg aaaaactgga tgataatctg | 780 |
| attcgcgatg aaattattac ctttctgagt gcaggccata taccaccag tagttttctg | 840 |
| agttggacct ttttcgaact ggcccgcaat ccggatgtgg aacagaaaat tctgcaggaa | 900 |
| attgtgaatg ccggcattaa gccgggtgaa attccgagta ccgaacaggt ggccaaatgt | 960 |
| aaatatattg atatggttat caaggagagc ctgcgctttc atagcccgat tccgctggtt | 1020 |
| attaagtatt gtcagaatga ttgcaccatt aagaccagtg aaggtaaaga atatgaaatt | 1080 |
| aagcgcggcc agctggccca gattcagatt agcgccgtgc ataaagatcc gaaactgtgg | 1140 |
| gaaaatccga atgtgtttga tccggaacgc tttaatccgg aaaaagaagc agatcgtcat | 1200 |
| ccgtgtgcat ggattccgtt tagcgatggt ccgcgtgcct gcattggtcg ccagtttagc | 1260 |
| ctgcaggaag gtaaactggc cctgattatg ctgctgtgca aatttcgttt tcgtctgctg | 1320 |
| gatgaaacca agaagtgggt tatcagatt attgtgagcc tgaaaccggt ggatctgatt | 1380 |
| atgaaagtgc tgccggcaga actgccgagt ccgaatgccg gcagcgatac cagtagtgtg | 1440 |
| aaagataccg ttaaaccgca gctgaaaccg aaagaaaatg aagtgctgga acatgcccgt | 1500 |
| tttccgctgc cgccggttac ctttctgtat ggtacccaga ccggcaccag tgaagaatat | 1560 |
| gcacgcaaac tgagtggtca ggcaaaagaa tttggcttta ccgatattgc cgtggcagaa | 1620 |
| ctggatgatt gggaagttgt taaaaataat cgtatcccga gtaataaggg tcagagtagt | 1680 |
| ccgagcgatg aagatggcac caaagtgagc cagctggctg ttattgttac cgcaacctat | 1740 |
| aatggttatc cgccggataa tgcactgaaa tttgatagct ggctgaccga tattaccaaa | 1800 |

```
gatcagaaaa atcagctgga aggtctgctg tatgccgtgt ttggttgtgg caataagcag   1860
tggcagagca cctttcaggc atttccgaaa aaagtggatg ccagtattga actgctgggc   1920
gcagaacgtc tggtgccggc aggcgcaggc aatgccgatc aggatattga tggtgacttt   1980
accaattgga gtgccagctt tgggccgca ctgatgcaga atatggccg cggcgccagt     2040 gataaagatg ccgatctgat gaccaccagt ggcccggtgg ccgatccgag taatgatttt   2100
accctggaat ttctgccgct gggtggtgac caggcagcaa tggaagcagc cctgggtaat   2160
cgtaatagcg atccgggcgc acaggtggcc attctggaaa ataaggaact gcaggatgtt   2220
gaaaaaagtg gccgtagtac ccgccatatt gttgttgaat gccgccggc cagcccgggc    2280 agtggtaaaa aagcaagtta cgcgccggt gaccatctgg aaattaagcc gtataatgat    2340
gatcagctgg tggaaaatat tgccattggc tttggctatg ttctggatag tgttttttcag  2400 attaaggatt gcaaaatcac caatctgagt ccgcgcagtc tggccgccaa tattattggt   2460
ccgtgcaccg ttcgcaatgc cctgacctat tttgccgatc tgagtggtcc gccgaccccgc  2520 tataccctga ccgtgatggc aaaacagctg gaaaaaccc gccgatgt ggcagaacgt      2580 ttactgcatg cactgcagcc gggcaaagaa accccgcgcc tgcgcgaatt tctgagtacc   2640
catcgtacca ttctggatat tcagcgcgcc tttaaaatta aggaactgag ctttaaagag   2700
ttcctgagca gtgttaatgt tattgttccg cgccgctata gtattagcag cggcccgctg   2760
gaacatccga tgaagtgag tgtgaccgtg gtgttgtta aagatattgg cggtgcagat     2820
aataataccg attattatgg tctggccagt ggttatctga tgcgctgccc gattggtagt   2880
aaaattgatg ccaaaattaa gccgtgcaaa ataatttttc gcctgccgga aaatgaacag   2940
accccggtta tttttatttg cgccggcacc ggctttgccc cgtttcgtgg ttttctgcag   3000
gaacgccatg ccaaaggttg aaaagtaaa gaaaaggcg gtagtagcga tgcatatctg     3060
tttttcggct gtcgtcatcc ggatcatgat tttatctatc agaaagaact ggaagaatac   3120
ctggaagatg gtaccctgac caaactgtat accaccttta ccgctataa tcagaccaaa    3180 aaatatgtgc agcatctgct gctgacccat gcccagctgc tgtttaatct gattatgaat   3240
gaaaacgcaa acatctatgt gtgtggtgca ggccgtggca tggcccatga tgtgcgccgc   3300 accttttgaac gcctggcagt tcaggttgca ggcatgagcg aaccggaagc cgtggatgcc   3360
attagtcaca tggttgatgc cgaacgctat aatgaagatg tttggggtta a             3411
```

<210> SEQ ID NO 5
<211> LENGTH: 1135
<212> TYPE: PRT
<213> ORGANISM: Umbelopsis isabellina

<400> SEQUENCE: 5

```
Met Thr Val Tyr Glu Ser Asp Lys Ile Pro Gly Pro Glu Pro Arg Val
1               5                   10                  15

Leu Leu Gly Asn Ile Pro Asp Val Tyr Pro Asp Phe Val Gly Asn Ile
            20                  25                  30

Thr Gln Leu His Glu Lys Tyr Gly Pro Val Met Arg Leu Tyr Leu Gly
        35                  40                  45

Gly His Asp Tyr Val Ser Val Cys Asp Pro Asp Cys Leu Gln Thr Thr
    50                  55                  60

His Lys Asp Gly Glu Tyr Phe Thr Lys Glu Ile Gln Ser Thr Tyr Glu
65                  70                  75                  80

Asp Leu Ala Ile Leu Asn Gly Arg Gly Leu Val Thr Thr Ala Thr Lys
                85                  90                  95
```

```
Asp Pro Asp Trp Ile Leu Gly His Lys Leu Leu Met Pro Ala Phe Ser
            100                 105                 110

Ala Arg Ala Met Lys Ala Tyr His Tyr Lys Met Gly Asp Thr Ile Lys
        115                 120                 125

Asp Leu Leu Asn Ile Ile Glu Ser Phe Gln Lys Ser Gly Glu Asp Phe
    130                 135                 140

Asp Val Ser Arg Trp Met Ile Ala Leu Ala Leu Glu Ser Ile Gly Asn
145                 150                 155                 160

Ile Gly Phe Asp Tyr Asp Phe Asn Leu Leu Lys Asp Pro Asn Ala Glu
                165                 170                 175

Arg His Pro Phe Thr Val Ala Leu Ser Tyr Val Gln Ser Met Ile Met
            180                 185                 190

Lys Arg Ser Ala Ser Val Ser Trp Met Lys Trp Met Lys Thr Ser Ala
        195                 200                 205

Asn Ala Arg Phe Gln Arg Asp Leu Gly Thr Leu Arg Asn Thr Leu Asp
    210                 215                 220

Ser Val Leu Lys Glu Arg His Glu His Pro His Ser Glu Asp Gln Gln
225                 230                 235                 240

Ser Asp Leu Leu Asp Phe Met Ile Ser Ala Ser Thr Lys Glu Gly Asp
                245                 250                 255

Lys Leu Asp Asp Lys Ile Ile Arg Asp Asn Val Met Thr Phe Leu Ser
            260                 265                 270

Ala Gly His Asn Thr Thr Ser Ser Phe Leu Ser Trp Thr Ile Leu Glu
        275                 280                 285

Leu Cys Arg His Pro Glu Val Ala Ala Thr Ile Arg Gln Glu Leu Ala
    290                 295                 300

Asn Ala Gly Val Gln Pro Gly Glu Ile Pro Thr Pro Glu Gln Val Asn
305                 310                 315                 320

Ala Cys Lys Tyr Leu Asp Leu Val Ile Lys Glu Ser Leu Arg Met His
                325                 330                 335

Pro Pro Ile Val Ala Val Leu Lys Tyr Cys Lys Asp Cys Thr Ile
            340                 345                 350

Lys Ala Gly Thr Thr Gly Asp Glu Tyr Lys Ile Lys Ala Gly Gln Leu
        355                 360                 365

Leu Gln Ser Asn Ile Asn Ala Leu His His Ser Thr Lys Val Trp Asp
    370                 375                 380

Glu Pro Met Val Phe Asn Pro Asp Arg Phe Ala Asp Ala Glu Leu His
385                 390                 395                 400

Pro Asn Ala Trp Met Pro Phe Ser Asp Gly Pro Arg Ala Cys Ile Gly
                405                 410                 415

Arg Gln Phe Ser Leu Gln Glu Gly Lys Leu Ala Leu Val Met Met Leu
            420                 425                 430

Ser Lys Phe Asn Phe Ser Met Glu Asp Pro Ser Gln Lys Ile Gly Tyr
        435                 440                 445

Glu Ile Ile Val Ala Ile Lys Pro Val Gly Leu Met Val Lys Val Thr
    450                 455                 460

Pro Ala Glu Leu Pro Glu Pro Thr Glu Ile Val Thr Gln Arg
465                 470                 475                 480

Arg Glu Ser Lys Ala Glu Pro Gln Glu Ser Leu Lys Pro Ala Glu Phe
                485                 490                 495

Pro Leu Pro Pro Val Thr Ile Leu Tyr Gly Thr Gln Thr Asn Thr Ser
            500                 505                 510
```

```
Glu Glu Tyr Ala Lys Lys Leu Ser Gly Gln Ala Lys Glu Phe Gly Phe
            515                 520                 525
Lys Thr Ile Lys Val Asp Asp Leu Asp Asn Trp Lys Leu Leu Asn Gly
        530                 535                 540
Gly Lys Leu Thr Lys Leu Asn Lys Asp Gln Ser Ala Pro Ser Ser Gly
545                 550                 555                 560
Asp Asp Val Lys Val Ser Glu Leu Val Val Val Thr Ala Thr Tyr
                565                 570                 575
Asn Gly Asn Pro Pro Asp Asn Ala Met Lys Phe Asp Glu Trp Leu Ser
                580                 585                 590
Lys Lys Thr Glu Ser Ile Glu Asp Thr Lys Ser Asn Glu Leu Glu Gly
        595                 600                 605
Ile Leu Tyr Ala Val Phe Gly Cys Gly Asn Arg Asp Trp Ser Ser Thr
        610                 615                 620
Phe Gln Lys Phe Pro Thr Ala Val Asp Thr Gly Leu Glu Leu Leu Gly
625                 630                 635                 640
Gly Glu Arg Leu Leu Pro Ala Gly Val Gly Asp Ala Ser Asp Asp Ile
                645                 650                 655
Asp Gly Asp Phe Ser Glu Trp Ser Ala Asn Phe Trp Ser Thr Leu Met
                660                 665                 670
Gln Arg Tyr Gly Gln Ser Ser Ser Gly Lys Asn Ala Asp Ile Met Thr
            675                 680                 685
Ser Thr Ala Pro Leu Ala Asp Pro Ser Lys Asp Phe Asn Leu Glu Phe
        690                 695                 700
Leu Pro Val His Lys Asn Lys Glu Leu Val Thr Gln Ala Asn Glu Asn
705                 710                 715                 720
Arg Asn Gln Arg Gly Lys Thr Val Thr Ile Lys Glu Asn Arg Glu Leu
                725                 730                 735
Gln Asn Ile Glu Lys Ser His Arg Ser Thr Lys His Ile Glu Val Gln
            740                 745                 750
Phe Asp Lys Ser Glu Asp Gly Lys Pro Leu Tyr Ile Ala Gly Asp His
        755                 760                 765
Leu Glu Ile Thr Pro Val Asn Lys Glu Glu Leu Val Glu Leu Val Ala
        770                 775                 780
Val Asn Leu Gly Leu Val Leu Asp Ser Val Phe Gln Ile Gln Met Asn
785                 790                 795                 800
Glu Val Asp Ile Ser His Leu Ser Pro Arg Ser Leu Ala Ala Asn Ile
                805                 810                 815
Lys Gly Pro Cys Thr Ile Arg Asn Ala Leu Lys Tyr Tyr Ala Asp Leu
                820                 825                 830
Thr Gly Pro Pro Thr Arg Tyr Thr Leu Ser Val Leu Gly Lys Gln Leu
                835                 840                 845
Glu Lys Thr Arg Pro Glu Ile Ala Lys Arg Leu Gln Glu Ala Leu Gln
            850                 855                 860
Pro Gly Lys Glu Thr Pro Arg Leu Lys Glu Phe Leu Ser Thr His Arg
865                 870                 875                 880
Thr Phe Val Asp Ile Met Lys Ala Phe Asn Ile Lys Glu Leu Asn Phe
                885                 890                 895
Lys Glu Phe Leu Ser Ser Val Asn Cys Ile Val Pro Arg Lys Tyr Ser
                900                 905                 910
Ile Ser Ser Gly Pro Thr Glu His Pro Phe Asp Pro Ser Val Ser Ile
            915                 920                 925
```

```
Gly Ile Val Arg Asp Ile Gly Gly Pro Asp Gly Lys Thr Glu Tyr Arg
        930                 935                 940

Gly Leu Ala Ser Gly Tyr Leu Asp Thr Leu Lys Pro Gly Ser Gln Val
945                 950                 955                 960

Asn Ala Gln Ile Lys Asp Cys Lys Ser Thr Phe Arg Leu Pro Asp Asp
                965                 970                 975

Gly Ser Thr Pro Val Ile Phe Ile Cys Ala Gly Thr Gly Met Ser Pro
            980                 985                 990

Phe Arg Gly Phe Leu Gln Glu Arg  His Ala Gln Gly Leu  Lys Ser Ser
        995                 1000                 1005

Lys Lys Gly Gly Ser Ser Glu  Ala Tyr Met Phe Phe  Gly Cys Arg
    1010                1015                 1020

His Pro Asp Gln Asp Phe Ile  Tyr Lys Asp Glu Leu  Gln Ser Tyr
    1025                1030                 1035

Val Glu Asp Gly Thr Leu Thr  Glu Leu Tyr Thr Thr  Phe Ser Arg
    1040                1045                 1050

Ser Asn Gln Val Val Lys Tyr  Val Gln His Ser Leu  Leu Gln His
    1055                1060                 1065

Ala Gln Met Leu Tyr Glu Leu  Met Val Asp His Asn  Ala Lys Val
    1070                1075                 1080

Tyr Val Cys Gly Ser Ala Gly  Ser Met Ala Lys Asp  Val Lys Arg
    1085                1090                 1095

Thr Trp Glu Arg Ile Thr Val  Gln Met Ser Gly Met  Ser Glu Pro
    1100                1105                 1110

Glu Ala Glu Asp Leu Leu Lys  Glu Trp Ser Asp Lys  Gly Lys Tyr
    1115                1120                 1125

Asn Glu Asp Val Trp Gly Thr
    1130                1135

<210> SEQ ID NO 6
<211> LENGTH: 3408
<212> TYPE: DNA
<213> ORGANISM: Umbelopsis isabellina

<400> SEQUENCE: 6
atgaccgtgt atgaaagcga taaaattccg gtccggaaac cgcgcgttct gctgggtaat    60
attccggatg tttatccgga ttttgttggc aatattaccc agctgcatga aaaatatggt   120
ccggttatgc gtctgtatct gggcggccat gattatgtga gtgtttgtga tccggattgt   180
ctgcagacca cccataaaga tggtaatat tttaccaaag agatccagag cacctatgaa   240
gatctggcca ttctgaatgg ccgtggcctg gtgaccaccg ccaccaaaga tccggattgg   300
attctgggcc ataaactgct gatgccggca ttttcagccc gcgccatgaa agcctatcat   360
tataaaatgg gtgacaccat taaggatctg ctgaatatta ttgaaagttt tcagaagtcc   420
ggtgaagatt ttgatgttag ccgttggatg attgccctgg cactggaaag cattggcaat   480
attggttttg attatgattt caacctgctg aaagatccga tgccgaacg tcatccgttt    540 accgttgccc tgagttatgt tcagagtatg attatgaaac gcagtgcaag cgttagctgg   600
atgaaatgga tgaaaaccag tgccaatgcc gctttcagc gtgatctggg tacccctgcgc   660 aataccctgg atagtgtgct gaaagaacgc catgaacatc cgcatagcga agatcagcag   720
agcgatctgc tggattttat gattagtgcc agtaccaaag aaggcgataa actggatgat   780
aaaattattc gcgataacgt tatgaccttt ctgagcgcag gtcataatac caccagcagt   840
tttctgagtt ggaccattct ggaactgtgc cgtcatccgg aagttgccgc aaccattcgt   900
```

```
caggaactgg caaatgccgg tgtgcagccg ggtgaaattc cgaccccgga acaggtgaat      960
gcctgtaaat atctggatct ggttattaag gaaagcctgc gtatgcatcc gccgattgtg     1020
gcagttctga atattgtaa aaaggattgt accatcaagg ccggtaccac cggtgacgaa      1080
tataaaatta aggcaggcca gctgctgcag agcaatatta atgcactgca tcatagcacc     1140
aaagtttggg atgaaccgat ggttttttaat ccggatcgtt ttgccgatgc agaactgcat    1200
ccgaatgcct ggatgccgtt tagtgatggt ccgcgtgcct gtattggccg tcagtttagc     1260
ctgcaggaag gcaaactggc actggttatg atgctgagca aattcaattt tagcatggaa     1320
gatccgagcc agaaaattgg ctatgaaatt attgtggcca ttaagccggt gggcctgatg     1380
gtgaaagtga ccccggccga actgccggaa ccgaccgaag aaattgttgt tacccagcgc     1440
cgtgaaagta agcagaacc gcaggaaagt ctgaaaccgg ccgaatttcc gctgccgccg      1500
gttaccattc tgtatggcac ccagaccaat accagcgaag aatatgcaaa aaagctgagc     1560
ggccaggcca agaatttgg ttttaaaacc attaaggtgg atgatctgga taattggaaa     1620
ctgctgaatg gcggtaaact gaccaaactg aataaggatc agagtgcacc gagtagtggt    1680
gacgatgtga agtgagtga actggtggtg gttgttaccg caacctataa tggcaatccg     1740
ccggataatg caatgaaatt tgatgaatgg ctgagtaaaa agaccgaaag cattgaagat    1800
accaaaagca atgaactgga aggcattctg tatgcagttt ttggctgcgg caatcgtgat    1860
tggagcagta cctttcagaa atttccgacc gcagtggata ccggtctgga actgctgggc    1920
ggcgaacgtc tgctgccggc aggcgttggc gatgccagtg atgatattga tggcgatttt   1980
agcgaatgga gcgcaaattt ttggagtacc ctgatgcagc gttatggtca gagcagtagc    2040
ggcaaaaatg cagatattat gaccagcacc gcaccgctgg cagatccgag taaagatttt   2100
aatctggaat tctgccggt gcataaaaat aaggaactgg tgacccaggc aaatgaaaat    2160
cgcaatcagc gcggtaaaac cgtgaccatt aaggaaaatc gcgaactgca gaatattgaa    2220
aaaagccatc gtagtaccaa acatattgaa gttcagtttg ataagagcga agatggtaaa    2280
ccgctgtata ttgccggtga ccatctggaa attaccccgg ttaataagga agaactggtt    2340
gaactggtgg ccgttaatct gggtctggtg ctggatagcc tgtttcagat tcagatgaat    2400
gaagttgata ttagtcacct gagcccgcgc agtctggcag caaatattaa gggcccgtgc    2460
accattcgca atgcactgaa atattatgca gatctgaccg tccgccgac ccgttatacc    2520
ctgagtgtgc tgggtaaaca gctggaaaaa acccgtccgg aaaattgccaa acgtctgcag    2580
gaagccctgc agccgggcaa agaaacccg cgcctgaaag aatttctgag tacccatcgt    2640
accttttgttg atattatgaa agcattcaat atcaaggagc tgaatttaa agagttcctg    2700
agcagtgtga attgtattgt gccgcgcaaa tatagcatta gtagtggtcc gaccgaacat    2760
ccgtttgatc cgagcgtgag cattggtatt gttcgcgata ttggtggtcc ggatggcaaa    2820
accgaatatc gcggtctggc aagcggctat ctggatacccc tgaaaccggg tagtcaggtg    2880
aatgcgcaga ttaaggattg taaagtacc tttcgcctgc cggatgatgg tagcaccccg     2940
gttatttta tttgcgccgg taccggcatg agcccgtttc gtggcttcct gcaggaacgc     3000
catgcccagg gtctgaaaag cagtaaaaaa ggtggcagta gtgaagcata tatgttttc     3060
ggttgccgcc atccggatca ggattttatc tataaagatg aactgcagag ttacgttgaa    3120
gatggtaccc tgaccgaact gtataccacc tttagtcgta gtaatcaggt ggttaaatat    3180
gtgcagcata gcctgctgca gcatgcacag atgctgtatg aactgatggt ggatcataat    3240
gcaaaagttt atgtttgtgg cagcgccggt agcatggcaa aagatgttaa acgcacctgg    3300
```

```
gaacgcatta ccgttcagat gagtggcatg agcgaaccgg aagccgaaga tctgctgaaa    3360
gaatggagcg ataaaggcaa atataatgaa gatgtgtggg gcacctaa                 3408
```